(12) United States Patent
Hoang et al.

(10) Patent No.: US 11,098,079 B2
(45) Date of Patent: Aug. 24, 2021

(54) CHARGED DEPTH FILTRATION OF ANTIGEN-BINDING PROTEINS

(71) Applicant: AMGEN INC., Thousand Oaks, CA (US)

(72) Inventors: Hai Hoang, Somerville, MA (US); Rafael Gonzalez, Thousand Oaks, CA (US); Junfen Ma, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 343 days.

(21) Appl. No.: 15/751,231

(22) PCT Filed: Aug. 12, 2016

(86) PCT No.: PCT/US2016/046929
§ 371 (c)(1),
(2) Date: Feb. 8, 2018

(87) PCT Pub. No.: WO2017/027861
PCT Pub. Date: Feb. 16, 2017

(65) Prior Publication Data
US 2018/0230180 A1 Aug. 16, 2018

Related U.S. Application Data

(60) Provisional application No. 62/204,831, filed on Aug. 13, 2015.

(51) Int. Cl.
| | |
|---|---|
| *C07K 1/36* | (2006.01) |
| *C07K 1/18* | (2006.01) |
| *C07K 1/113* | (2006.01) |
| *C07K 1/34* | (2006.01) |
| *B01D 15/36* | (2006.01) |
| *B01D 15/38* | (2006.01) |
| *C07K 1/22* | (2006.01) |
| *C07K 16/28* | (2006.01) |
| *G01N 27/447* | (2006.01) |

(52) U.S. Cl.
CPC .............. *C07K 1/36* (2013.01); *B01D 15/362* (2013.01); *B01D 15/3809* (2013.01); *C07K 1/1133* (2013.01); *C07K 1/18* (2013.01); *C07K 1/22* (2013.01); *C07K 1/34* (2013.01); *C07K 16/2887* (2013.01); *C07K 2317/40* (2013.01); *G01N 27/44791* (2013.01)

(58) Field of Classification Search
CPC combination set(s) only.
See application file for complete search history.

(56) References Cited

U.S. PATENT DOCUMENTS

| | | | |
|---|---|---|---|
| 6,596,172 B1 | 7/2003 | Kopf | |
| 7,157,276 B2 | 1/2007 | Pham | |
| 7,759,117 B2 | 7/2010 | Pham | |
| 7,855,280 B2 | 12/2010 | Coffman et al. | |
| 8,491,904 B2 | 7/2013 | Hickman | |
| 8,895,709 B2 | 11/2014 | Hickman et al. | |
| 8,946,395 B1 | 2/2015 | Herigstad et al. | |
| 9,243,056 B2 | 1/2016 | Moeller et al. | |
| 9,249,182 B2 | 2/2016 | Herigstad et al. | |
| 9,333,481 B2 * | 5/2016 | Koehler | B01J 20/08 |
| 2006/0024298 A1 * | 2/2006 | Lazar | C07K 16/2893 424/133.1 |
| 2010/0056759 A1 | 3/2010 | Paglia | |
| 2012/0157664 A1 * | 6/2012 | Schotte | C07K 16/18 530/387.3 |
| 2012/0168381 A1 * | 7/2012 | Ramaswamy | B01D 39/18 210/663 |
| 2012/0208986 A1 | 8/2012 | Wenger et al. | |
| 2012/0238730 A1 | 9/2012 | Dong et al. | |
| 2012/0264920 A1 | 10/2012 | Wang et al. | |

(Continued)

FOREIGN PATENT DOCUMENTS

| | | |
|---|---|---|
| EP | 2627425 A1 | 8/2013 |
| JP | 2010533192 A | 10/2010 |

(Continued)

OTHER PUBLICATIONS

Kotia et al. "Analysis of monoclonal antibody product heterogeneity resulting from alternate cleavage sites of signal peptide" Analytical Biochemistry 399 (2010) 190-195 (Year: 2010).*

Zhang et al. "Method development and validation of capillary sodium dodecyl sulfate gel electrophoresis for the characterization of a monoclonal antibody" Journal of Pharmaceutical and Biomedical Analysis 53 (2010) 1236-1243 (Year: 2010).*

Hapuarachchi et al., Use of capillary electrophoresis-sodium dodecyl sulfate to monitor disulfide scrambled forms of an Fc fusion protein during purification process, *Anal. Biochem.* 414:187-95 (2011).

(Continued)

*Primary Examiner* — Daniel E Kolker
*Assistant Examiner* — James L Rogers
(74) *Attorney, Agent, or Firm* — Marshall, Gerstein & Borun LLP

(57) ABSTRACT

Methods of producing an aqueous formulation of an antigen-binding protein or enhancing re-oxidation of an antigen-binding protein are disclosed. The methods comprise (a) contacting an aqueous solution comprising antigen-binding protein molecules with a charged depth filter under conditions sufficient to enhance re-oxidation of the antigen-binding protein molecules and achieve a decrease in the percentage of reduced antigen-binding protein molecules, compared to the percentage of reduced antigen-binding protein molecules observed prior to step (a); and (b) optionally, measuring the amount or relative amount of reduced antigen-binding protein molecules. Formulations comprising a re-oxidized antigen-binding protein are also described.

40 Claims, 10 Drawing Sheets
Specification includes a Sequence Listing.

(56) References Cited

U.S. PATENT DOCUMENTS

| | | |
|---|---|---|
| 2013/0012689 A1 | 1/2013 | Singh et al. |
| 2013/0034876 A1 | 2/2013 | Roy et al. |
| 2013/0273607 A1 | 10/2013 | O'Connor |
| 2013/0336957 A1 | 12/2013 | Wang et al. |
| 2014/0010820 A1 | 1/2014 | Wang et al. |
| 2014/0141021 A1 | 5/2014 | Chtourou et al. |
| 2014/0154270 A1 | 6/2014 | Wang et al. |
| 2014/0348845 A1 | 11/2014 | Bill, Jr. et al. |
| 2015/0065696 A1 | 3/2015 | Wang et al. |
| 2015/0079074 A1 | 3/2015 | Garidel et al. |
| 2015/0133636 A1 | 5/2015 | Xenopoulos et al. |
| 2016/0115194 A1 | 4/2016 | Gagnon |
| 2016/0176921 A1 | 6/2016 | Rajendran et al. |

FOREIGN PATENT DOCUMENTS

| | | | | |
|---|---|---|---|---|
| JP | 2013044748 A | 3/2013 | | |
| WO | WO-2008036899 A2 * | 3/2008 | ........... | A61L 2/0017 |
| WO | WO-2014/100443 A2 | 6/2014 | | |
| WO | WO-2015/059478 A1 | 4/2015 | | |
| WO | WO-2015/070068 A1 | 5/2015 | | |
| WO | WO-2015/130222 A1 | 9/2015 | | |
| WO | WO-2015/142777 A1 | 9/2015 | | |
| WO | WO-2015/198320 A1 | 12/2015 | | |

OTHER PUBLICATIONS

International Preliminary Report on Patentability, PCT/US2016/046929 (dated Feb. 13, 2018).
International Search Report and Written Opinion, PCT/US2016/046929 (dated Nov. 9, 2018).
Liu et al., Recovery and purification process development for monoclonal antibody production, *mAbs*. 2:480-99 (2010).
Millistak® Pod Disposable Depth Filter System 2009.
Roush et al., Advances in Primary Recovery: Centrifugation and Membrane Technology. Biotechnology Progress, Apr. 15, 2008, vol. 24, No. 3, pp. 488-495.
Hutterer et al., "Monoclonal antibody disulfide reduction during manufacturing", Landes Bioscience. 5:4, 608-613, Jul./Aug. 2013.

* cited by examiner

SEQUENCE LISTING

```
<160> NUMBER OF SEQ ID NOS: 12

<210> SEQ ID NO 1
<211> LENGTH: 451
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Heavy Chain

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Light Chain

<400> SEQUENCE: 2

Gln Ile Val Leu Ser Gln Ser Pro Ala Ile Leu Ser Ala Ser Pro Gly
1               5                   10                  15
```

```
Glu Lys Val Thr Met Thr Cys Arg Ala Ser Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Val Ala Ala Pro
             100                 105                 110

Ser Val Phe Ile Phe Pro Pro Ser Asp Glu Gln Leu Lys Ser Gly Thr
             115                 120                 125

Ala Ser Val Val Cys Leu Leu Asn Asn Phe Tyr Pro Arg Glu Ala Lys
         130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                 165                 170                 175

Thr Leu Thr Leu Ser Lys Ala Asp Tyr Glu Lys His Lys Val Tyr Ala
             180                 185                 190

Cys Glu Val Thr His Gln Gly Leu Ser Ser Pro Val Thr Lys Ser Phe
             195                 200                 205

Asn Arg Gly Glu Cys
    210

<210> SEQ ID NO 3
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR1

<400> SEQUENCE: 3

Ser Tyr Asn Met
1

<210> SEQ ID NO 4
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR2

<400> SEQUENCE: 4

Ala Ile Tyr Pro Gly Asn Gly Asp Thr Ser Tyr Asn Gln Lys Phe Lys
1               5                   10                  15

Gly

<210> SEQ ID NO 5
<211> LENGTH: 11
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<223> OTHER INFORMATION: HC CDR3

<400> SEQUENCE: 5

Ser Thr Tyr Tyr Gly Gly Asp Trp Tyr Phe Asn
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR1

<400> SEQUENCE: 6

Arg Ala Ser Ser Ser Val Ser Tyr Ile His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR2

<400> SEQUENCE: 7

Ala Thr Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR3

<400> SEQUENCE: 8

Gln Gln Trp Thr Ser Asn Pro Pro Thr
1               5

<210> SEQ ID NO 9
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 9

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60
```

```
Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser
        115
```

<210> SEQ ID NO 10
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 10

```
Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Phe Val Gly Ser Ser
                 20                  25                  30

Ile His Trp Tyr Gln Gln Arg Thr Asn Gly Ser Pro Arg Leu Leu Ile
             35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys
            100                 105
```

<210> SEQ ID NO 11
<211> LENGTH: 122
<212> TYPE: PRT
<213> ORGANISM: Homo Sapiens

<400> SEQUENCE: 11

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asn Asp Tyr
                 20                  25                  30

Ala Met His Trp Val Arg Gln Ala Pro Gly Lys Gly Leu Glu Trp Val
             35                  40                  45

Ser Thr Ile Ser Trp Asn Ser Gly Ser Ile Gly Tyr Ala Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120
```

<210> SEQ ID NO 12
<211> LENGTH: 106

```
<212> TYPE: PRT
<213> ORGANISM: Homo Sapiens

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Asn Trp Pro Ile Thr
                85                  90                  95

Phe Gly Gln Gly Thr Arg Leu Glu Ile Lys
                100                 105
```

CHARGED DEPTH FILTRATION OF ANTIGEN-BINDING PROTEINS

CROSS-REFERENCE TO RELATED APPLICATION

The benefit under 35 U.S.C. § 119(e) of U.S. Provisional Patent Application No. 62/204,831 filed Aug. 13, 2016, is hereby claimed and the disclosure thereof is incorporated herein by reference.

SEQUENCE LISTING

This application contains, as a separate part of the disclosure, a sequence listing in computer-readable form (49841A_SeqListing.txt; 11,962 bytes bytes; created Aug. 12, 2016), which is incorporated by reference in its entirety.

FIELD OF THE INVENTION

The present disclosure relates to methods of producing an aqueous formulation comprising a re-oxidized antigen-binding protein.

BACKGROUND OF THE INVENTION

Therapeutic antigen-binding proteins such as antibodies are currently used to treat millions of patients world-wide. Antigen-binding protein molecules are typically produced in mammalian cell culture systems and recovered using a standard series of filtration and chromatography steps (see, e.g., Liu et al., *mAbs*. 2(5): 480-499 (2010)). The structure and stability of antigen-binding protein molecules depend heavily on the disulfide bonds that link the two heavy chains and the heavy and light chains in each antigen-binding protein molecule, however, during the production and purification process, one or more disulfide bonds can be reduced to free thiol groups. Reduction of the inter-chain disulfide bonds weakens the structural integrity of the antigen-binding protein molecule and can lead to antigen-binding protein fragments (e.g., light chain, heavy chain, and their combinations) and/or antigen-binding protein aggregates, which impair the biological functions of the antigen-binding proteins and consequently, their therapeutic efficacy. Even if reduced molecules remain intact during the purification process via other forces (e.g., ionic, hydrophobic, hydrogen bonds, and Van der Waals), they may fragment during storage or in clinical use. Thus, there is a need for methods of re-oxidizing partially reduced antigen-binding protein molecules to produce stable and effective pharmaceutical formulations.

SUMMARY OF THE INVENTION

The present disclosure is directed to methods of producing an aqueous formulation of an antigen-binding protein (such as an antigen-binding protein comprising an Fc region, an antibody, or a peptibody) or enhancing re-oxidation of such an antigen-binding protein and to formulations comprising a re-oxidized antigen-binding protein prepared according to these methods. In one aspect, the disclosure provides a method of producing an aqueous formulation of an antigen-binding protein (such as an antigen-binding protein comprising an Fc region, an antibody, or a peptibody) comprising (a) contacting an aqueous solution comprising antigen-binding protein molecules with a charged depth filter under conditions sufficient to achieve at least a 20% decrease, optionally a 30% or 40% decrease, in the percentage of reduced antigen-binding protein molecules, compared to the percentage of reduced antigen-binding protein molecules observed prior to step (a); and (b) optionally, measuring the amount (such as the total amount) or relative amount of reduced antigen-binding protein molecules. In another aspect, the disclosure provides a method of enhancing re-oxidization of an antigen-binding protein (such as an antigen-binding protein comprising an Fc region, an antibody, or a peptibody) comprising (a) contacting an aqueous solution comprising antigen-binding protein molecules with a charged depth filter under conditions sufficient to enhance re-oxidation of the antigen-binding protein molecules; and (b) optionally, measuring the amount (such as the total amount) or relative amount of reduced antigen-binding protein molecules. In one aspect, the amount (such as the total amount) or relative amount of reduced antigen-binding protein molecules is measured using non-reduced capillary electrophoresis with sodium dodecyl sulfate (nrCE-SDS). In any of the preceding aspects, the total amount of reduced antigen-binding protein molecules after contact with the charged depth filter in step (a) is 10% or less of the total amount of antigen-binding protein molecules and/or is decreased by at least three-fold compared to before step (a).

In some aspects, step (a) of the methods described herein is followed by and/or preceded by subjecting the aqueous solution of antigen-binding protein molecules to Protein A chromatography. Optionally, a method according to the disclosure further comprises a step of inactivating one or more viruses in the aqueous solution of antigen-binding protein molecules and/or subjecting the aqueous solution of antigen-binding protein molecules to cation exchange chromatography and/or sparging air or oxygen into the aqueous solution of antigen-binding protein molecules. Optionally, a method further comprises adding an inhibitor of thioredoxin or thioredoxin-like protein to the aqueous solution of antigen-binding protein molecules (see, e.g., U.S. Patent Publication No. 20090053786).

In one aspect, a method of producing an aqueous formulation of an antigen-binding protein (such as an antigen-binding protein comprising an Fc region, an antibody, or a peptibody) comprises contacting an aqueous solution comprising antigen-binding protein molecules with a charged depth filter under conditions sufficient to achieve at least a 20% decrease in the percentage of reduced antigen-binding protein molecules, compared to the percentage of reduced antigen-binding protein molecules observed prior to the contacting step, wherein the at least 20% decrease is determined using non-reduced capillary electrophoresis with sodium dodecyl sulfate (nrCE-SDS). In another aspect, a method of enhancing re-oxidization of an antigen-binding protein (such as an antigen-binding protein comprising an Fc region, an antibody, or a peptibody) comprising contacting an aqueous solution comprising antigen-binding protein molecules with a charged depth filter under conditions sufficient to achieve at least a two-fold increase in re-oxidation of the antigen-binding protein molecules following the contacting step, wherein the at least two-fold increase is determined using non-reduced capillary electrophoresis with sodium dodecyl sulfate (nrCE-SDS).

In some aspects, a method described herein comprises (1) a Protein A chromatography step, optionally followed by charged depth filtration; (2) a viral inactivation step, optionally followed by charged depth filtration; and (3) a cation exchange chromatography step, optionally followed by charged depth filtration; further optionally comprising one or more of (4) a chromatography step optionally selected from salt-intolerant interaction chromatography, hydrophobic interaction chromatography, and mixed mode chromatography, optionally followed by charged depth filtration; (5) a virus filtration step, optionally followed by charged depth filtration; and (5) ultrafiltration and/or diafiltration, optionally followed by charged depth filtration. Optionally, in any of the methods described herein, following contact with a charged depth filter, the filtrate is incubated, for example, at least about 1, 2, 3, 4, 5, 6, 7, 8, 9, 10, 12, 24 or more hours.

In one aspect, the charged depth filter comprises a diatomaceous earth layer. Optionally, the charged depth filter further comprises a cellulose layer and/or an inorganic layer, such as an inorganic layer comprises a polyamine resin. In another aspect, the charged depth filter comprises a positive ion, such as any one of sodium, calcium, magnesium, mercury, chromium, aluminum, potassium, lead, arsenic, cadmium, cobalt, iron, manganese, titanium, zinc, nickel, copper, or combinations thereof. In another aspect, the charged depth filter comprises one of the following combinations of positive ions: 1) copper and cobalt, 2) copper and cadmium, 3) cobalt and cadmium, or 4) copper, cobalt, and cadmium. In some embodiments, the positive ion is a metal with a $^{+}2$ or higher oxidation state (such as $^{+}3$ or $^{+}4$). In some aspects, the method comprises contacting an aqueous solution comprising antigen-binding protein molecules with one, two, three, four, five, or more charged depth filter(s).

In one aspect, the aqueous solution comprises an antigen-binding protein molecule which is an IgG antibody, such as an IgG1 or IgG2 antibody. For example, in some aspects, the antibody is an IgG1 antibody with a kappa light chain or an IgG1 antibody with a lambda light chain.

In some aspects, the antigen-binding protein binds an antigen selected from the group consisting of CD3, CD4, CD8, CD19, CD20, CD34, HER2, HER3, HER4, the EGF receptor, LFA-1, Mol, p150, p95, VLA-4, ICAM-1, VCAM, alpha v/beta 3 integrin, vascular endothelial growth factor, growth hormone, thyroid stimulating hormone, follicle stimulating hormone, luteinizing hormone, growth hormone releasing factor, parathyroid hormone, mullerian-inhibiting substance, human macrophage inflammatory protein, erythropoietin, NGF-beta, platelet-derived growth factor, aFGF, bFGF, epidermal growth factor, TGF-alpha, TGF-beta1, TGF-beta2, TGF-beta3, TGF-beta4, TGF-beta5, IGF-I, IGF-II, des(1-3)-IGF-I, insulin, insulin A-chain, insulin B-chain, proinsulin, insulin-like growth factor binding proteins, factor VIII, tissue factor, von Willebrand factor, protein C, alpha-1-antitrypsin, plasminogen activators, urokinase, tissue plasminogen activator, bombazine, thrombin, thrombopoietin, M-CSF, GM-CSF, G-CSF, albumin, IgE, flk2/flt3 receptor, obesity receptor, bone-derived neurotrophic factor, NT-3, NT-4, NT-5, NT-6, relaxin A-chain, relaxin B-chain, prorelaxin, interferon-alpha, interferon-beta, interferon-gamma, IL-1 to IL-10, AIDS envelope viral antigen, calcitonin, glucagon, atrial natriuretic factor, lung surfactant, tumor necrosis factor-alpha, tumor necrosis factor-beta, enkephalinase, RANTES, mouse gonadotropin-associated peptide, Dnase, inhibin, activin; protein A, protein D, bone morphogenetic protein, superoxide dismutase, decay accelerating factor, and combinations thereof.

In another aspect, the aqueous formulation comprises an antibody selected from the group consisting of abciximab, adalimumab, alemtuzumab, basiliximab, belimumab, bevacizumab, brentuximab vedotin, canakinumab, cetuximab, certolizumab pegol, daclizumab, denosumab, eculizumab, efalizumab, gemtuzumab, golimumab, ibritumomab tiuxetan, infliximab, ipilimumab, muromonab-CD3, natalizumab, nivolumab, ofatumumab, omalizumab, palivizumab, panitumumab, ranibizumab, rituximab, tocilizumab, tositumomab, trastuzumab, ustekinumab, vedolizumab, and a biosimilar of any of the foregoing. In one embodiment, the aqueous formulation comprises rituximab or an antibody comprising 1, 2, 3, 4, 5, or 6 of the complementarity determining regions (CDRs) of rituximab, for example, the antibody can comprise (a) a light chain containing all three light chain CDRs of rituximab, (b) a heavy chain containing all three heavy chain CDRs of rituximab, or (c) both. In another embodiment, the aqueous formulation comprises infliximab or an antibody comprising 1, 2, 3, 4, 5, or 6 of the complementarity determining regions (CDRs) of infliximab, for example, the antibody can comprise (a) a light chain containing all three light chain CDRs of infliximab, (b) a heavy chain containing all three heavy chain CDRs of infliximab, or (c) both. In one embodiment, the aqueous formulation comprises ofatumumab or an antibody comprising 1, 2, 3, 4, 5, or 6 of the complementarity determining regions (CDRs) of ofatumumab, for example, the antibody can comprise (a) a light chain containing all three light chain CDRs of ofatumumab, (b) a heavy chain containing all three heavy chain CDRs of ofatumumab, or (c) both.

In another aspect, the disclosure provides a formulation comprising a re-oxidized antigen-binding protein molecule (such as an antigen-binding protein comprising an Fc region, a fusion protein, an antibody, an antibody fragment or a peptibody) prepared using any of the methods described herein.

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

DETAILED DESCRIPTION OF THE INVENTION

Figure 1:
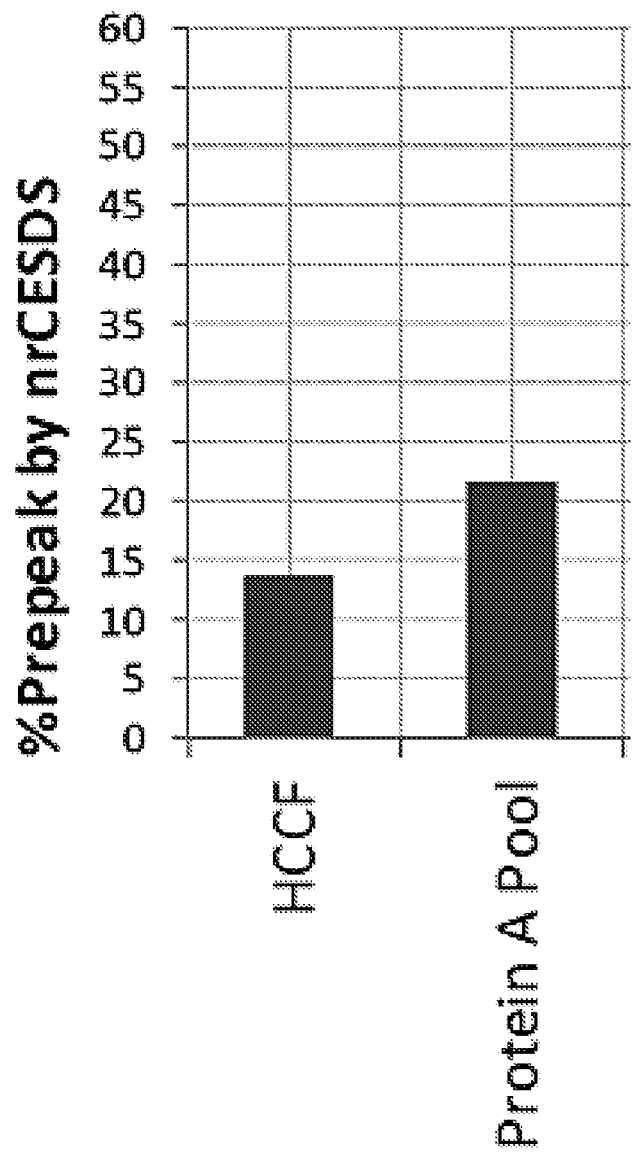
FIG. 1 depicts the level of partial antibody reduction as the percentage of pre-peak species measured using nrCE-SDS in the harvested cell culture fluid (HCCF), and in the Protein A Pool.

The present invention is based, at least in part, on the surprising discovery that material from a charged depth filter promotes the re-oxidation of antigen-binding molecules at least three-fold more than an uncharged depth filter control. Use of charged depth filtration to promote re-oxidation is particular desirable for antigen-binding molecules prone to reduction, such as IgG1 antibodies.

The present disclosure provides methods of producing an aqueous formulation of an antigen-binding protein (such as an antigen-binding protein comprising an Fc region, an antibody, or a peptibody) or enhancing re-oxidation of an antigen-binding protein comprising contacting an aqueous solution comprising antigen-binding protein molecules with a charged depth filter under conditions sufficient to decrease the percentage of reduced antigen-binding protein molecules. The disclosure also provides formulations comprising a re-oxidized antigen-binding protein (such as an antigen-binding protein comprising an Fc region, an antibody, or a peptibody) prepared using the methods described herein. The methods comprising a charged depth filter according to the present disclosure are more effective than other methods such as sparging with air, chilling, and sterile membrane filtration, for decreasing the amount of partially reduced antigen-binding protein molecules in the aqueous solution and thus remedy the fragmentation and aggregation issues that mar antigen-binding protein production processes and the resulting pharmaceutical formulations.

The following definitions may be useful in aiding the skilled practitioner in understanding the disclosure. Unless otherwise defined herein, scientific and technical terms used in the present disclosure shall have the meanings that are commonly understood by those of ordinary skill in the art. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. Any and all of the embodiments described for antibodies may also be used for an antigen binding protein, such as an antigen-binding protein comprising an Fc region (e.g., a peptibody). Conversely, any and all of the embodiments described for antigen-binding proteins also specifically apply, in each and every instance, to antibodies as defined herein.

The term "antigen-binding protein" refers to a protein or polypeptide that comprises an antigen-binding region or antigen-binding portion that has a strong affinity for another molecule to which it binds (antigen). Antigen-binding proteins encompass antibodies, peptibodies, antibody fragments, antibody derivatives, antibody analogs, fusion proteins (including single-chain variable fragments (scFvs) and double-chain (divalent) scFvs), and antigen receptors including chimeric antigen receptors (CARs).

The term "antibody" is used herein in accordance with its ordinary meaning in the biochemical and biotechnological arts. Among antibodies within the meaning of the term as it is used herein are those isolated from biological sources, including monoclonal and polyclonal antibodies, antibodies made by recombinant DNA techniques (also referred to at times herein as recombinant antibodies), including those made by processes that involve activating an endogenous gene and those that involve expression of an exogenous expression construct, including antibodies made in cell culture and those made in transgenic plants and animals, and antibodies made by methods involving chemical synthesis, including peptide synthesis and semi-synthesis. Also within the scope of the term as it is used herein, except as otherwise explicitly set forth, are chimeric antibodies, humanized antibodies, and multivalent (e.g., bispecific) antibodies, among others. The prototypical IgG antibody is a tetrameric glycoprotein comprised of two identical light chain-heavy chain dimers joined together by disulfide bonds. There are two types of vertebrate light chains, kappa and lambda. Each light chain is comprised of a constant region and a variable region. The kappa and lambda light chains are distinguished by their constant region sequences. There are five types of vertebrate heavy chains: alpha, delta, epsilon, gamma, and mu. Each heavy chain is comprised of a variable region and a constant region, which usually comprise three domains. The five heavy chain types define five classes of vertebrate antibodies (isotypes): IgA, IgD, IgE, IgG, and IgM. There are four human IgG subclasses, IgG1, IgG2, IgG3, and IgG4, and two IgA subclasses, IgA1 and IgA2, for example. In some embodiments, the antibody is a full-length antibody. All of these and others not specifically described above are included in the meaning of the term "antibody" or "antibodies" as used herein.

The term "charged depth filter" or "depth filter" refers to a filter comprising a) porous matrix (e.g., 2 mm to 5 mm thick matrix) that filters a solution based on physical capture within the matrix channels and/or electrokinetic adsorption, e.g., due to a charge on the matrix. A variety of positively charged ions, preferably metal ions, are suitable for use in such a filter. Charged depth filters are available commercially from, for example, Cuno, Inc. (e.g., ZETA PLUS S series, ZETA PLUS SP series, ZETA PLUS LP series, ZETA PLUS CP series, ZETA PLUS LP BC series), EMD Millipore (e.g., D0HC, C0HC, F0HC, A1HC, B1HC, X0HC), Sartorius AG, and Pall Corporation (e.g., SEITZ P series, SEITZ K series, SUPRADUR series, STAX series, SUPRACAP Series, SUPRAPAK series, SUPRADISC series).

The term "complementarity determining region" or "CDR" refers to a hypervariable region of a light or heavy chain of an antigen-binding protein, typically about 9 to 12 amino acids in length, that confer binding specificity to the antigen-binding protein.

In one aspect, the disclosure provides a method of producing an aqueous formulation of an antigen-binding protein (such as an antigen-binding protein comprising an Fc region, a fusion protein, an antibody, an antibody fragment, or a peptibody) comprising (a) contacting an aqueous solution comprising antigen-binding protein molecules with a charged depth filter under conditions sufficient to achieve at least a 20% decrease in the percentage of reduced antigen-binding protein molecules, compared to the percentage of reduced antigen-binding protein molecules observed prior to step (a); and (b) optionally, measuring the amount (such as the total amount) or relative amount of reduced antigen-binding protein molecules. In another aspect, the disclosure provides a method of enhancing re-oxidation of an antigen-binding protein (such as an antigen-binding protein comprising an Fc region, a fusion protein, an antibody, an antibody fragment or a peptibody) comprising (a) contacting an aqueous solution comprising antigen-binding protein molecules with a charged depth filter under conditions sufficient to enhance re-oxidation of the antigen-binding protein molecules; and (b) optionally, measuring the amount of relative amount of reduced antigen-binding protein molecules. Re-oxidation of antigen-binding protein molecules (such as antigen-binding proteins comprising an Fc region, fusion proteins, antibodies, antibody fragments or peptibodies) can be evidenced by a decrease in the amount (such as the total amount) or relative amount (e.g., percentage) of reduced antigen-binding protein molecules, compared to the amount (such as the total amount) or relative amount (e.g., percentage) of reduced antigen-binding protein molecules observed prior to step (a).

The decrease in reduced antigen-binding protein molecules can be measured, for example, by quantifying the amount of antigen-binding protein fragments in the aqueous solution before and after contact with the charged depth filter to assess the degree of inter-chain disulfide bond breakage. One method of identifying size variants and quantifying the amount of partially reduced antigen-binding protein molecules in a sample comprises using nrCE-SDS to determine the percentage of pre-peak species corresponding to antigen-binding protein fragments (see, e.g., Guo et al., *Electrophoresis.* 29(12):2550-6 (2008)). Generally, non-reducing buffer is added to a sample. After incubation at high temperature, the samples are injected into a silica capillary. The separation is performed using a capillary electrophoresis sodium dodecyl sulfate (CE-SDS) gel, and effective voltage and detection is performed, for example, at 220 nm by UV absorbance. Other methods for measuring the purity of an aqueous formulation of an antigen-binding protein, e.g., size exclusion chromatography (SEC), differentiate between protein aggregates and monomers, but do not distinguish between partially reduced and re-oxidized antigen-binding protein molecules in a sample and thus are not sufficient for use in the methods of the present disclosure.

In one aspect, a method of producing an aqueous formulation of an antigen-binding protein (such as an antigen-binding protein comprising an Fc region, an antibody, or a peptibody) comprises contacting an aqueous solution comprising antigen-binding protein molecules with a charged depth filter under conditions sufficient to achieve at least a 20% decrease in the percentage of reduced antigen-binding protein molecules, compared to the percentage of reduced antigen-binding protein molecules observed prior to the contacting step, wherein the at least 20% decrease is determined using nrCE-SDS. In another aspect, a method of enhancing re-oxidization of an antigen-binding protein (such as an antigen-binding protein comprising an Fc region, an antibody, or a peptibody) comprising contacting an aqueous solution comprising antigen-binding protein molecules with a charged depth filter under conditions sufficient to achieve at least a two-fold increase in re-oxidation of the antigen-binding protein molecules following the contacting step, wherein the at least two-fold increase is determined using nrCE-SDS.

In some aspects, the percentage of reduced antigen-binding protein (such as an antigen-binding protein comprising an Fc region, an antibody, or a peptibody) molecules or reduced disulfide bonds in the aqueous solution comprising antigen-binding protein molecules is decreased by at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 45%, at least 50%, at least 55%, at least 60%, at least 65%, at least 70%, at least 75%, at least 80%, at least 85%, at least 90%, or more, following contacting the aqueous solution with a changed depth filter according to the disclosure, compared to the percentage of reduced antigen-binding protein molecules or reduced disulfide bonds observed prior to the contacting step. In one aspect, the total amount of reduced antigen-binding protein molecules after contacting an aqueous solution comprising antigen-binding protein molecules with a charged depth filter is less than 10%, for example, less than 9%, less than 8%, less than 7%, less than 6%, less than 5%, less than 4%, less than 3%, less than 2%, or less than 1%, of the total amount of antigen-binding protein molecules in the solution. As another measure, the percentage of reduced antigen-binding protein molecules or reduced disulfide bonds in the aqueous solution comprising disulfide bonds is decreased by at least about 1.5 fold, for example, at least about 1.5-fold, at least about 2-fold, at least about 2.5-fold, at least about 3-fold, at least about 4-fold, at least about 5-fold, or more, after the aqueous solution is contacted with a charged depth filter as disclosed, compared to before the contacting step.

In some aspects, a charged depth filter according to the disclosure comprises at least one diatomaceous earth layer and/or a positively charged ion, preferably a metal ion. In some exemplary aspects, the diatomaceous earth layer comprises a high percentage (e.g., about 90%) of silica and/or is calcinated to remove organic matter. Optionally, the charged depth filter further comprises a cellulose layer and/or an inorganic layer. In any of the aspects, the inorganic layer optionally comprises a resin binder that provides wet strength, for example, a polyamine resin such as polyamidoamine-epichlorohydrin (PAAE). In some embodiments, the charge depth filter comprises at least one metal ion selected from the group consisting of sodium, calcium, magnesium, mercury, chromium, cadmium, aluminum, potassium, lead, arsenic, cobalt, iron, manganese, titanium, zinc, nickel, copper, and combinations thereof. In another aspect, the charged depth filter comprises one of the following combinations of metals: 1) copper and cobalt, 2) copper and cadmium, 3) cobalt and cadmium, or 4) copper, cobalt, and cadmium. In some embodiments, the metal (or one or more or all metals in a combination of metals) has a $^{+}2$ or higher oxidation state (such as $^{+}3$ or $^{+}4$). Charged depth filters suitable for use in the methods of the disclosure include, but are not limited to, the MILLISTAK+ A1HC and X0HC filters (EMD Millipore, Billerica, Mass.), and the ZETA PLUS (e.g., ZETA PLUS 30SP) filter (Cuno, Inc., Meriden, Conn.). One or more of the metals (such as copper) on the charged depth filter may promote re-oxidation. In some aspects, a charged depth filter according to the disclosure comprises one or more of the following media: HC, CE, DE, IM, CR, ZA, SP, HP, ZC, ELIS, LA, LP, EKS-P, EKM-P, SUPRA EK 1 P, KS 50 P, SUPRA 80 P, K 100 P. K 250 P, K 700 P, and K 900 P.

Protocols for charged depth filtration are known in the art and are also available from the manufacturers of commercial charged depth filters. In some aspects, the charged depth filter is flushed with de-ionized water and equilibration buffer prior to loading the aqueous solution comprising antigen-binding protein molecules. Optionally, the aqueous solution comprising antigen-binding protein molecules is loaded into the charged depth filter system to achieve a throughput between about 10 L/m$^2$ and about 1000 L/m$^2$, for example, between about 350 L/m$^2$ and about 850 L/m$^2$, between about 250 L/m$^2$ and about 450 L/m$^2$, between about 150 L/m$^2$ and about 450 L/m$^2$ between about 50 L/m$^2$ and about 800 L/m$^2$, or about 150 L/m$^2$, about 200 L/m$^2$, about 250 L/m$^2$, about 300 L/m$^2$, about 350 L/m$^2$, about 400 L/m$^2$, about 450 L/m$^2$, about 500 L/m$^2$, about 550 L/m$^2$, about 600 L/m$^2$, about 650 L/m$^2$, about 700 L/m$^2$, about 750 L/m$^2$, about 800 L/m$^2$, about 850 L/m$^2$, or about 900 L/m$^2$. In some aspects, the flow rate of the aqueous solution through the charged depth filter system is less than about 500 L/m$^2$/h, for example, less than about 400 L/m$^2$/h, less than about 300 L/m$^2$/h, less than about 200 L/m$^2$/h, less than about 100 L/m$^2$/h, or less than about 50 L/m$^2$, optionally at a pressure less than or equal to about 50 psi, for example, about 50 psi, less than about 50 psi, less than about 40 psi, less than about 30 psi, less than about 20 psi, or less than about 10 psi. In one aspect, the total amount of the aqueous solution comprising antigen-binding protein molecules is filtered through the charged depth filter system over about 5 hours or less, for example, about 5 hours, about 4.5 hours, about 4 hours, about 3.5 hours, about 3 hours, about 2.5 hours, about 2 hours, about 1.5 hours, about 1 hour, about 30 minutes, or less. In some embodiments, the total amount of the aqueous solution comprising antigen-binding protein molecules is filtered through the charged depth filter system over a time period of between about 1 and about 3 hours, such as about 1 to 2 hours, or about 1.5 to 2 hours.

In one aspect, the aqueous solution comprising antigen-binding protein molecules is contacted with a charged depth filter at room temperature, i.e., about 20° C. to about 26° C., for example, at about 20° C., about 21° C., about 22° C., about 23° C., about 24° C., about 25° C., or about 26° C. In another aspect, the contacting step occurs at a temperature between about 1° C. or 2° C. and about 8° C., for example, at about 2° C., about 3° C., about 4° C., about 5° C., about 6° C., about 7° C., or about 8° C.

In some embodiments, a charged depth filter or material from a charged depth filter (such as the diatomaceous earth layer) is tested for the ability to re-oxidize an antigen-binding protein using any of the methods described herein. In some embodiments, the antigen-binding protein is incubated with a charged depth filter or material from a charged depth filter (such as the diatomaceous earth layer) and then samples of the antigen-binding protein are taken at various time points (such as every 30 minutes for 1 or 2 hours) to measure the amount of reduced antigen-binding protein. In some embodiments, material from a charged depth filter (such as the diatomaceous earth layer) is placed into a column and the antigen-binding protein is loaded onto the column and pushed through the column. The amount of reduced antigen-binding protein is measured for samples collected from the column.

In some aspects, a method according to the disclosure further comprises subjecting the aqueous solution comprising antigen-binding protein molecules to Protein A chromatography. Techniques for Protein A chromatography are known in the art, and the process is routinely used to remove contaminants such as host cell protein, DNA, and viruses from a solution comprising antigen-binding protein molecules with an Fc region based on the affinity of Protein A for the Fc and/or Fab region of immunoglobulins. In some embodiments, a neutral or basic loading buffer (such as pH 7 to 8) is used to bind the antigen-binding protein onto the Protein A resin. In some embodiments, low pH is used to elute the antigen-binding protein from the Protein A resin, such as a pH between 3 and 5, such as 3 to 4, or 4 to 5. In one embodiment, the aqueous solution comprising antigen-binding protein molecules is subjected to Protein A chromatography before being contacted with a charged depth filter. In some embodiments, after Protein A chromatography, the aqueous solution comprising antigen-binding protein molecules is incubated for at least 1, 2, 3, 4, 5, 6, 7, 8, 9, 10, 12, 15, 20, 24, or more hours before being contacted with a charged depth filter. In some embodiments, after protein A chromatography, the aqueous solution comprising antigen-binding protein molecules is incubated for between 2 and 10 hours (such as between 2 to 24 hours, 4 to 20 hours, or 4 to 10 hours) before being contacted with a charged depth filter. In another embodiment, the aqueous solution comprising antigen-binding protein molecules is first contacted with a charged depth filter and then afterwards subjected to Protein A chromatography. In some embodiments, after depth filtration, the aqueous solution comprising antigen-binding protein molecules is incubated for at least 1, 2, 3, 4, 5, 6, 7, 8, 9, 10, 12, 15, 20, 24, 32, 48 or more hours to promote re-oxidation before being subjected to protein A chromatography. In some embodiments, after depth filtration, the aqueous solution comprising antigen-binding protein molecules is incubated for between 2 and 32 hours (such as between 12 to 24 hours, 24 to 48 hours, or 24 to 32 hours) before being subjected to protein A chromatography.

A method of the disclosure further comprises a step of inactivating one or more viruses present in the aqueous solution comprising antigen-binding protein molecules. In one embodiment, the method comprises inactivating one or more viruses in an aqueous solution comprising antigen-binding protein molecules before contacting the solution with a charged depth filter. In another embodiment, a method comprises inactivating one or more viruses in an aqueous solution comprising antigen-binding protein molecules after contacting the solution with a charged depth filter. In some embodiments, a virus-inactivated aqueous solution comprising antigen-binding protein molecules is incubated for at least 1, 2, 3, 4, 5, 6, 7, 8, 9, 10, 12, 15, 20, 24, 32, 48 or more hours following charged depth filtration to promote re-oxidation. Methods for inactivating viruses are known in the art and generally comprise lowering the pH of an aqueous solution comprising antigen-binding protein molecules, e.g., to a pH between 3.0 and 4.0, for an extended period of time, such as about one hour. In some embodiments, a method according to the disclosure comprises subjecting an aqueous solution comprising antigen-binding protein molecules to Protein A chromatography and a viral inactivation step, e.g., Protein A chromatography followed by viral inactivation, before being contacted with a charged depth filter. In another embodiment, the aqueous solution comprising antigen-binding protein molecules is subjected to Protein A chromatography and a viral activation step, e.g., Protein A chromatography followed by viral inactivation, after being contacted with a charged depth filter. In yet another embodiment, the aqueous solution comprising antigen-binding protein molecules is subjected to Protein A chromatography, followed by being contacted with a charged depth filter, followed by viral inactivation. In one embodiment, the aqueous solution comprising antigen-binding protein molecules is subjected to Protein A chromatography, followed by viral inactivation, and then contacted with a charged depth filter, followed by an incubation hold time of at least about 1, 2, 3, 4, 5, 6, 7, 8, 9, 10, 12, 14, 16, 18, 20, 24 or more hours.

In still another aspect, a method of the disclosure further comprises subjecting an aqueous solution comprising antigen-binding protein molecules to cation exchange (CEX) chromatography. Techniques for CEX chromatography are known in the art, and the process is routinely used to separate antibodies such as a human or humanized IgG1 and IgG2 antibodies based on the affinity of the antibodies for the negatively charged CEX resin. In one embodiment, the aqueous solution comprising antigen-binding protein molecules is subjected to CEX chromatography before being contacted with a charged depth filter. In another embodiment, the aqueous solution comprising antigen-binding protein molecules is first contacted with a charged depth filter and then subjected to CEX chromatography. In still another embodiment, an aqueous solution comprising antigen-binding protein molecules is subjected to Protein A chromatography and a viral inactivation step and then contacted with a charged depth filter, optionally with an incubation hold time of at least about 1, 2, 3, 4, 5, 6, 7, 8, 9, 10, 12, 14, 16, 18, 20, 24 or more hours followed charged depth filtration, before being subjected to CEX chromatography. In another embodiment, an aqueous solution comprising antigen-binding protein molecules is subjected to Protein A chromatography followed by CEX chromatography before being contacted with a charged depth filter.

In one aspect, a method according to the disclosure comprises contacting an aqueous solution comprising antigen-binding protein molecules with one charged depth filter. In another aspect, an aqueous solution comprising antigen-binding protein molecules is contacted with more than one charged depth filter, for example, two, three, four, or more charged depth filters, e.g., in series or in parallel or separated by other process steps such as centrifugation, microfiltration, ultrafiltration, diafiltration, Protein A chromatography, cation exchange chromatography, anion exchange chromatography, and/or viral inactivation/filtration. In some aspects, an aqueous solution comprising antigen-binding protein molecules (e.g., HCCF) is optionally contacted with a charged depth filter and then subjected to a Protein A chromatography step, optionally followed by a charged depth filtration step, then subjected to a viral inactivation step, optionally followed by a charged depth filtration step, then subjected to a cation exchange chromatography step, optionally followed by a charged depth filtration step, then subjected to another chromatography step, optionally selected from salt-intolerant interaction chromatography with primary amine ligand (STIC PA), hydrophobic interaction chromatography (HIC), and mixed mode chromatography (MMC), optionally followed by a charged depth filtration step, then subjected to a virus filtration step, optionally followed by a charged depth filtration step, then subjected to an ultra/diafiltration step, optionally followed by a charged depth filtration step. Further optionally, there is an incubation hold time of at least about 1, 2, 3, 4, 5, 6, 7, 8, 9, 10, 12, 14, 16, 18, 20, 24 or more hours followed any charged depth filtration step.

In one aspect of any of the methods described herein, the effect of enhancing re-oxidation of the antigen-binding protein molecules continues for an extended period of time after the aqueous solution of antigen-binding protein molecules is contacted with the charged depth filter. In some aspects, the percentage of reduced antigen-binding protein molecules continues to decrease for at least one hour, for example, at least two hours, at least three hours, at least four hours, at least five hours, or more, following charged depth filtration, eventually reaching a steady state amount of reduced antigen-binding protein molecules that is minimal, e.g., after about 4 to about 24 hours. In some aspects, the percentage of reduced antigen-binding protein molecules in the aqueous solution continues to reduce at a temperature between about 2° C. and room temperature. In contrast, the amount of partially reduced antigen-binding protein molecules in an aqueous solution of antigen-binding protein molecules continues to increase if the solution is not contacted with a charged depth filter (see Examples).

In one aspect, the aqueous solution of antigen-binding protein molecules is further contacted with a composition comprising diatomaceous earth. Optionally, the composition comprises diatomaceous earth that is acid washed and/or contains about 90% silicon dioxide. Examples of compositions comprising diatomaceous earth include, but are not limited to, Celite 545 Filter Aid (Fisher Scientific, Pittsburgh, Pa.) and HYFLO SUPERCEL (Sigma-Aldrich, St. Louis, Mo.).

In one aspect, the aqueous solution of antigen-binding protein molecules is further contacted with a positive ion in solution, for example, a metal ion such as sodium, calcium, magnesium, mercury, molybdenum, chromium, cadmium, aluminum, potassium, cobalt, iron, manganese, titanium, zinc, nickel, copper, or combinations thereof. In one aspect, the aqueous solution of antigen-binding protein molecules is further contacted with a one of the following combinations of metals: 1) copper and cobalt, 2) copper and cadmium, 3) cobalt and cadmium, or 4) copper, cobalt, and cadmium. In some embodiments, the metal (or one or more or all of the metals in a combination of metals) has a $^{+}2$ or higher oxidation state (such as $^{+}3$ or $^{+}4$). In one aspect, the positive ion, e.g., a dissolved metal ion, is added to an aqueous solution comprising antigen-binding protein molecules before or during the step of contacting the aqueous solution with a charged depth filter. For example, copper is optionally added into HCCF. Optionally, the aqueous solution comprising antigen-binding protein molecules is sparged with air or oxygen, i.e., before, during, and/or after contacting the aqueous solution with a charged depth filter. Also optionally, the dissolved oxygen level in the bioreactor is increased, the HCCF vessel is prefilled with oxygen saturated buffer before collection of HCCF, and/or aeration in the bioreactor and/or HCCF vessel is increased.

In one aspect, a method of producing an aqueous formulation of an antigen-binding protein (such as an antigen-binding protein comprising an Fc region, a fusion protein, an antibody, or a peptibody) or of enhancing re-oxidation of such an antigen-binding protein comprises (a) contacting an aqueous solution comprising antigen-binding protein molecules with at least one extractable from a charged depth filter under conditions sufficient to achieve at least a 20% decrease, optionally a 30% or 40% decrease, in the percentage of reduced antigen-binding protein molecules, compared to the percentage of reduced antigen-binding protein molecules observed prior to step (a); and (b) optionally, measuring the amount (such as the total amount) or relative amount of reduced antigen-binding protein molecules. An extractable from a charged depth filter can be, for example, a positive ion described herein or other component present in the charged depth filter. Optionally, the extractable is removed from a charged depth filter by contacting the charged depth filter with an acidic solution, e.g., $H_2SO_4$. In one aspect, the aqueous solution of antigen-binding protein molecules is contacted with at least one extractable from a charged depth filter in lieu of being contacted with a charged depth filter. In another aspect, the aqueous solution of antigen-binding protein molecules is contacted with at least one extractable from a charged depth filter in addition to being contacted with a charged depth filter.

In some embodiments, antigen-binding proteins according to the present disclosure comprise heavy and light chain polypeptides that have the same amino acid sequence as those that occur in and constitute naturally-occurring antibodies, and/or those that are made by hybridoma technologies, by activation of an endogenous gene (by homologous or non-homologous recombination, for instance), by expression of an exogenous gene under the control of an endogenous transcription control region, by expression of an exogenous expression construct, by semi-synthesis and by de novo synthesis, to name some techniques commonly employed for making antigen-binding proteins in accordance with the disclosure.

Included among these antigen-binding proteins are those in whole or part having a de novo amino acid sequence, those having an amino acid sequence that matches in some way that of a naturally occurring antibody, but differs from it in other ways, those that have the same but different amino acid sequences as a naturally occurring counterpart or sequence relating thereto, but differ from the counterpart in one or more post-translational modifications, and those comprised in part of any of the foregoing (in part or in whole) fused to one or more polypeptide regions that can be of or derived from or related to a second, different antigen-binding protein polypeptide, and can be of or derived from any other polypeptide or protein, whether naturally occurring, resembling but differing therefrom, having a semi-de novo amino acid sequence and/or a de novo sequence, among others, as long as the antigen-binding protein structure comprises a disulfide bond that is capable of being reduced. Such polypeptides are generally referred to herein as fusion polypeptides and/or fusion proteins. For example, antigen-binding proteins according to the disclosure are proteins comprising one or more CDRs and/or CDR-derived and/or CDR-related regions of a naturally occurring or commercially available antigen-binding protein.

In some examples, antigen-binding proteins as used herein includes "peptibodies" comprising one or more antigen-specific peptides (e.g., two or three peptides in series) fused to an Fc region of an antibody. See, e.g., Shimamoto, *MAbs.* 4(5):586-91 (2012); U.S. Patent Publication 2014/0024111, published Jan. 23, 2014.

Further among antigen-binding proteins in accordance with the disclosure are modified proteins in accordance with all of the foregoing. Included among such modified proteins are proteins modified chemically by a non-covalent bond, covalent bond, or both a covalent and non-covalent bond. Also included are all of the foregoing further comprising one or more post-translational modifications which may be made by cellular modification systems or modifications introduced ex vivo by enzymatic and/or chemical methods, or introduced in other ways.

Regarding antigen-binding proteins in accordance with the foregoing and with other aspects of the disclosure, see, for example, *Protein Engineering: Principles and Practice*, Jeffrey L. Cleland and Charles S. Craik, eds. Wiley-Liss, Inc., New York (1996), particularly therein Kelley, Robert F., "Engineering Therapeutic Antibodies," Chapter 15, pp. 399-434 and Hollinger, P. & Hudson, P., "Engineered antibody fragments and the rise of single domains," *Nature Biotechnology*, September 2005, 1126-1136, each of which is herein incorporated by reference in its entirety, particularly in parts pertinent to the structure and engineering of antigen-binding proteins, particularly biopharmaceutical antibodies and antibody-related pharmaceutical proteins in accordance with the disclosure.

In one aspect, the antigen-binding protein belongs to a class particularly sensitive to reduction. In some embodiments, the antigen-binding protein is an IgG1 or IgG2 antibody. In some embodiments, the antibody has a lambda light chain. In some embodiments, the antibody is selected from the group consisting of IgG1λ, IgG1κ, IgG2λ, and IgG2κ.

As to all of the foregoing, particularly preferred are human, humanized, and other antigen-binding proteins, such as human and humanized antibodies, that do not engender significantly deleterious immune responses when administered to a human. Also preferred are antigen-binding proteins in accordance with all the foregoing that similarly do not cause a significantly deleterious immune responses when administered to non-humans, e.g., domesticated mammals.

In some embodiments, the antibody is selected from the group consisting of proteins that bind specifically to one or more CD proteins, HER receptor family proteins, cell adhesion molecules, growth factors, nerve growth factors, fibroblast growth factors, transforming growth factors (TGF), insulin-like growth factors, osteoinductive factors, insulin and insulin-related proteins, coagulation and coagulation-related proteins, colony stimulating factors (CSFs), other blood and serum proteins blood group antigens; receptors, receptor-associated proteins, growth hormone receptors, T-cell receptors; neurotrophic factors, neurotrophins, relaxins, interferons, interleukins, viral antigens, lipoproteins, integrins, rheumatoid factors, immunotoxins, surface membrane proteins, transport proteins, homing receptors, addressins, regulatory proteins, and immunoadhesins.

For example, in some aspects, an antigen-binding protein according to the disclosure binds to one of more of the following, alone or in any combination: (i) CD proteins including but not limited to CD3, CD4, CD8, CD19, CD20, and CD34; (ii) HER receptor family proteins, including, for instance, HER2, HER3, HER4, and the EGF receptor; (iii) cell adhesion molecules, for example, LFA-1, Mol, p150,95, VLA-4, ICAM-1, VCAM, and alpha v/beta 3 integrin; (iv) growth factors, including but not limited to, for example, vascular endothelial growth factor ("VEGF"); growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), transforming growth factors (TGF), including, among others, TGF-alpha and TGF-beta, including TGF-beta1, TGF-beta2, TGF-beta3, TGF-beta4, or TGF-beta5, insulin-like growth factors-I and -II (IGF-I and IGF-II), des(1-3)-IGF-I (brain IGF-I), and osteoinductive factors; (v) insulins and insulin-related proteins, including but not limited to insulin, insulin A-chain, insulin B-chain, proinsulin, and insulin-like growth factor binding proteins; (coagulation and coagulation-related proteins, such as, among others, factor VIII, tissue factor, von Willebrand factor, protein C, alpha-1-antitrypsin, plasminogen activators, such as urokinase and tissue plasminogen activator ("t-PA"), bombazine, thrombin, and thrombopoietin; (vii) colony stimulating factors (CSFs), including the following, among others, M-CSF, GM-CSF, and G-CSF; (viii) other blood and serum proteins, including but not limited to albumin, IgE, and blood group antigens; (ix) receptors and receptor-associated proteins, including, for example, flk2/flt3 receptor, obesity (OB) receptor, growth hormone receptors, and T-cell receptors; (x) neurotrophic factors, including but not limited to, bone-derived neurotrophic factor (BDNF) and neurotrophin-3, -4, -5, or -6 (NT-3, NT-4, NT-5, or NT-6); (xi) relaxin A-chain, relaxin B-chain, and prorelaxin; (xii) interferons, including for example, interferon-alpha, -beta, and -gamma; (xiii) interleukins (ILs), e.g., IL-1 to IL-10; (xiv) viral antigens, including but not limited to, an AIDS envelope viral antigen; (xv) lipoproteins, calcitonin, glucagon, atrial natriuretic factor, lung surfactant, tumor necrosis factor-alpha and -beta, enkephalinase, RANTES (regulated on activation normally T-cell expressed and secreted), mouse gonadotropin-associated peptide, Dnase, inhibin, and activin; (xvi) integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, addressins, regulatory proteins, immunoadhesins, antigen-binding proteins; and (xvii) biologically active fragments or variants of any of the foregoing.

As to all of the foregoing, particularly preferred are those that are effective therapeutic agents, particularly those that exert a therapeutic effect by binding a target, particularly a target among those listed above, including targets derived therefrom, targets related thereto, and modifications thereof.

Optionally, the antigen-binding protein is selected from the group consisting of: antigen-binding proteins that bind any of: OPGL, myostatin, IL-4 receptor, IL1-R1, Ang2, NGF, CD22, IGF-1 receptor, B7RP-1, IFN gamma, TALL-1, stem cell factors, Flt-3, IL-17 or IL-17 receptor.

For example, in some aspects, an antibody or peptibody according to the disclosure can be characterized as follows: (i) OPGL specific antibodies and peptibodies (also referred to as RANKL specific antibodies, peptibodies), including fully humanized and human OPGL specific antibodies, particularly fully humanized monoclonal antibodies, including, but not limited to, the antibodies described in International Publication No. WO 03/002713, which is incorporated herein in its entirety as to OPGL specific antibodies, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4 of WO 03/002713, each of which is individually and specifically incorporated by reference herein in its entirety fully as disclosed in the foregoing publication; (ii) Myostatin binding agents or peptibodies, including myostatin specific peptibodies, particularly those described in US Application Publication No. 2004/0181033, which is incorporated by reference herein in its entirely particularly in parts pertinent to myostatin specific peptibodies, including, but not limited to, peptibodies of the mTN8-19 family, including TN8-19-1 through TN8-19-40, TN8-19 con1 and TN8-19 con2; peptibodies of the mL2 family; the mL15 family of SEQ ID NOS: 384-409; the mL17 family; the mL20 family; the mL21 family; the mL24 family, each of which is individually and specifically incorporated by reference herein in its entirety fully as disclosed in the foregoing publication; (iii) IL-4 receptor specific antibodies, particularly those that inhibit activities mediated by binding of IL-4 and/or IL-13 to the receptor, including those described in International Publication No. WO 2005/047331 of International Application No. PCT/US2004/03742, which is incorporated herein by reference in its entirety, particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L213; L2H14; L3H1; L4H1; L5H1; L6H1, each of which is individually and specifically incorporated by reference herein in its entirety fully as disclosed in the foregoing publication; (iv) Interleukin 1-receptor 1 ("IL1-R1") specific antibodies, peptibodies, including, but not limited to, those described in U.S. Application Publication No. US2004/097712A1 which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. application publication; (v) Ang2 specific antibodies and peptibodies, including, but not limited to, those described in International Publication No. WO 03/057134 and U.S. Application Publication No. US2003/0229023, each of which is incorporated herein by reference in its entirety particularly in parts pertinent to Ang2 specific antibodies and peptibodies, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1(C); L1(C) 1K; 2×L1 (C); Con4 (C); Con4 (C) 1K; 2×Con4 (C) 1K; Con4-L1 (N); Con4-L1 (C); TN-12-9 (N); C17 (N); TN8-8(N); TN8-14 (N); Con 1 (N), also including anti-Ang 2 antibodies and formulations such as those described in International Publication No. WO 2003/030833, which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1KAb1P; and Ab1P, in their various permutations as described therein, each of which is individually and specifically incorporated by reference herein in its entirety fully as disclosed in the foregoing publication; (vi) NGF specific antibodies, including, in particular, but not limited to those described in US Application Publication No. US2005/0074821, which is incorporated herein by reference in its entirety particularly as to NGF-specific antibodies, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication; (vii) CD22 specific antibodies, such as those described in U.S. Pat. No. 5,789,554 which is incorporated herein by reference in its entirety as to CD22 specific antibodies, particularly human CD22 specific antibodies, such as, but not limited to, humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0; (viii) IGF-1 receptor specific antibodies such as those described in International Patent Application No. PCT/US2005/046493, which is incorporated herein by reference in its entirety as to IGF-1 receptor specific antibodies, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52, each of which is individually and specifically incorporated by reference herein in its entirety fully as disclosed in the foregoing International Application; (ix) B-7 related protein 1 ("B7RP-1") specific antibodies, (B7RP-1 also is referred to in the literature as B7H2, ICOSL, B7h, and CD275) particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Provisional Application No. 60/700,265, filed 18 Jul. 2005, which is incorporated herein by reference in its entirety as to such antibodies, including but not limited to antibodies designated therein as follow: 16H; 5D; 2H; 43H; 41H; and 15H, each of which is individually and specifically incorporated by reference herein in its entirety fully as disclosed in the foregoing U.S. Provisional Application; (x) IL-15 specific antibodies or peptibodies, such as, humanized monoclonal antibodies, particularly antibodies such as those disclosed in U.S. Patent Publication Nos. US2003/0138421; US2003/023586; US2004/0071702, each of which is incorporated herein by reference in its entirety as to IL-15 specific antibodies and peptibodies, including particularly, for instance, but not limited to, HuMax IL-15 antibodies, such as, for instance, 146B7; (xi) IFN gamma specific antibodies, especially human IFN gamma specific antibodies, particularly fully human anti-IFN gamma antibodies, such as, for instance, those described in US Patent Publication No. US2005/0004353, which is incorporated herein by reference in its entirety as to IFN gamma specific antibodies, particularly, for example, the antibodies therein designated 1118; 1118*; 1119; 1121; and 1121* each of which is individually and specifically incorporated by reference herein in its entirety fully as disclosed in the foregoing US publication; (xii) TALL-1 specific antibodies and other TALL specific binding proteins such as those described in U.S. Patent Publication No. 2003/0195156 which is incorporated herein by reference in its entirety as to TALL-1 binding proteins, particularly the molecules of Tables 4 and 5B, each of which is individually and specifically incorporated by reference herein in its entirety fully as disclosed in the foregoing US publication; (xiii) CD20 specific antibodies, such as those described in U.S. Pat. Nos. 5,736,137 and 5,843,439; which are incorporated herein by reference in their entirety as to CD20 specific antibodies, particularly human CD20 specific antibodies, such as, but not limited to humanized and fully human antibodies, including but not limited to humanized and fully human monoclonal antibodies, particularly including but not limited to human CD20 specific IgG antibodies, including, but limited to, for example, the chimeric mouse/human CD20 specific antibody rituximab, CAS registry number 174722-31-7, and ofatumumab, CAS registry number 679818-59-8; (xiv) calcitonin gene-related peptide (CGRP) specific antibodies; (xv) platelet specific (e.g., platelet glycoprotein IIb/IIIa (PAC-1) specific) antibodies; (xvi) sclerostin specific antibodies; and (xvii) bispecific antibodies, for example, bispecific T cell engagers (BiTEs), including bispecific antibodies having affinity for any of the foregoing protein targets.

In some aspects, the antibody or peptibody is selected from the group consisting of proteins that bind specifically to one or more of: CD3, CD4, CD8, CD19, CD20, CD34; HER2, HER3, HER4, the EGF receptor; LFA-1, Mol, p150, 95, VLA-4, ICAM-1, VCAM, alpha v/beta 3 integrin; vascular endothelial growth factor (VEGF); growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), NGF-beta, platelet-derived growth factor (PDGF), aFGF, bFGF, epidermal growth factor (EGF), TGF-alpha, TGF-beta1, TGF-beta2, TGF-beta3, TGF-beta4, TGF-beta5, IGF-I, IGF-II, des(1-3)-IGF-I (brain IGF-I), insulin, insulin A-chain, insulin B-chain, proinsulin, insulin-like growth factor binding proteins; such as, among others, factor VIII, tissue factor, von Willebrand factor, protein C, alpha-1-antitrypsin, plasminogen activators, such as urokinase and tissue plasminogen activator (t-PA), bombazine, thrombin, and thrombopoietin; M-CSF, GM-CSF, G-CSF, albumin, IgE, flk2/flt3 receptor, obesity (OB) receptor, bone-derived neurotrophic factor (BDNF), NT-3, NT-4, NT-5, NT-6); relaxin A-chain, relaxin B-chain, prorelaxin; interferon-alpha, -beta, and -gamma; IL-1 to IL-10; AIDS envelope viral antigen; calcitonin, glucagon, atrial natriuretic factor, lung surfactant, tumor necrosis factor-alpha and -beta, enkephalinase, RANTES, mouse gonadotropin-associated peptide, Dnase, inhibin, and activin; protein A or D, bone morphogenetic protein (BMP), superoxide dismutase, and decay accelerating factor (DAF).

In some aspects, the antibody is selected from the group consisting of: abciximab, adalimumab, alemtuzumab, basiliximab, belimumab, bevacizumab, brentuximab vedotin, canakinumab, cetuximab, certolizumab pegol, daclizumab, denosumab, eculizumab, efalizumab, gemtuzumab, golimumab, ibritumomab tiuxetan, infliximab, ipilimumab, muromonab-CD3, natalizumab, nivolumab, ofatumumab, omalizumab, palivizumab, panitumumab, ranibizumab, rituximab, tocilizumab, tositumomab, trastuzumab, ustekinumab, vedolizumab, and a biosimilar of any of the foregoing. In one aspect, the antibody is rituximab (see, e.g., U.S. Pat. No. 5,843,439); or comprises a heavy chain variable region that is at least 90%, for example, at least 92%, at least 95%, at least 97%, or at least 99%, identical to SEQ ID NO: 1, and a light chain variable region that is at least 90%, for example, at least 92%, at least 95%, at least 97%, or at least 99%, identical to SEQ ID NO: 2; or comprises 1, 2, 3, 4, 5, or 6 of the CDRs of rituximab (SEQ ID NOs: 3-8). In another aspect, the antibody is infliximab (see, e.g., U.S. Pat. No. 6,284,471); or comprises a heavy chain variable region that is at least 90%, for example, at least 92%, at least 95%, at least 97%, or at least 99%, identical to SEQ ID NO: 9, and a light chain variable region that is at least 90%, for example, at least 92%, at least 95%, at least 97%, or at least 99%, identical to SEQ ID NO: 10. In another aspect, the antibody is ofatumumab (see, e.g., U.S. Pat. No. 8,529,902); or comprises a heavy chain variable region that is at least 90%, for example, at least 92%, at least 95%, at least 97%, or at least 99%, identical to SEQ ID NO: 11, and a light chain variable region that is at least 90%, for example, at least 92%, at least 95%, at least 97%, or at least 99%, identical to SEQ ID NO: 12.

Antigen-binding proteins according to the invention encompass all of the foregoing and further include variants that retain all of the heavy chain CDRs thereof, and/or all of the light chain CDRs thereof, and comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of an antigen-binding protein, as illustrated above, particularly a pharmaceutical binding protein, such as a GenBank or other reference sequence of a reference protein. Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

Particularly preferred variants in this regard have 50% to 150% of the activity of the aforementioned reference antigen-binding protein, particularly highly preferred embodiments in this regard have 60% to 125% of the activity of the reference antigen-binding protein, yet more highly preferred embodiments have 75% to 110% of the activity of the reference antigen-binding protein, still more highly preferred embodiments have 85% to 125% the activity of the reference, still more highly preferred embodiments have 90% to 110% of the activity of the reference.

In another aspect, the disclosure provides formulations comprising a re-oxidized antigen-binding protein molecule prepared using any of the methods described herein. Many reagents and methods conventionally employed for the formulation of pharmaceutical antigen-binding protein formulations can be used for the formulations in accordance with various aspects and preferred embodiments of the disclosure. In accordance therewith, many methods and ingredients for formulating and using pharmaceuticals that are well-known and routine in the pertinent arts can be used in designing, making, and using formulations in accordance with various aspects and preferred embodiments of the disclosure relating thereto. Such methods and ingredients are described in, for example, REMINGTON: THE SCIENCE AND PRACTICE OF PHARMACY, 21st Ed.; Beringer et al. Editors, Lippincott, Williams & Wilkins, Philadelphia, Pa. (2005); ANSEL'S PHARMACEUTICAL DOSAGE FORMS AND DRUG DELIVERY SYSTEMS, 8th Ed., Allen et al., Editors, Lippincott, Williams & Wilkins, Philadelphia, Pa. (2005); and PHARMACEUTICAL FORMULATION OF PEPTIDES AND PROTEINS, Sven Frokjaer and Lars Hovgaard, Editors, CRC Press, Boca Raton, Fla. (2000), each of which is herein incorporated in its entirety, particularly in parts pertinent to conventional ingredients and methods that may be used in a formulation comprising a re-oxidized antigen-binding protein molecule in accordance with various aspects and preferred embodiments of the invention relating thereto.

Additional methods and ingredients that can be useful in this regard are disclosed in, among others, U.S. Pat. No. 6,171,586; WO 2005/044854; U.S. Pat. Nos. 6,288,030; 6,267,958; WO 2004/055164; U.S. Pat. No. 4,597,966; US 2003/0138417; U.S. Pat. Nos. 6,252,055; 5,608,038; 6,875,432; US 2004/0197324; WO 02/096457; U.S. Pat. Nos. 5,945,098; 5,237,054; 6,485,932; 6,821,515; 5,792,838; 5,654,403; 5,908,826; EP 0 804 163; and WO 2005/063291, each of which is incorporated herein by reference in its entirety, particularly in parts pertinent to pharmaceutically acceptable antigen-binding protein formulations in accordance with the disclosure.

Various specific aspects of the ingredients and specific types of formulations are further described below, by way of illustration. The description thus provided is not exhaustive of the methods and compositions possible for aqueous formulations comprising a re-oxidized antigen-binding protein in accordance with the various aspects and embodiments of the disclosure, nor is it in any way exclusive.

Almost invariably, formulations comprising a re-oxidized antigen-binding protein in accordance with numerous aspects and embodiments of the disclosure will contain additional ingredients including, but not limited in any way to, excipients and other pharmaceutical agents. Formulations in accordance with various aspects and embodiments of the disclosure may contain, among others, excipients, as described below, including, but not limited to, ingredients for modifying, maintaining, or preserving, for example, osmolality, osmolarity, viscosity, clarity, color, tonicity, odor, sterility, stability, rate of dissolution or release, adsorption or penetration of the formulations and/or antigen-binding protein. Formulations will, of course, depend upon, for example, the particular antigen-binding protein being formulated, the other active agents, such as other pharmaceuticals, that will be comprised in the formulation, the intended route of administration, the method of administration to be employed, the dosage, the dosing frequency, and the delivery format, among others.

Formulations in accordance with certain of the preferred embodiments in various aspects of the invention provide compositions comprising a re-oxidized antigen-binding protein and a carrier. In some embodiments the concentration of the antigen-binding protein is between approximately, in mg/mL: 10 and 400, or 10 and 300, or 10 and 250, or 10 and 200, or 10 and 150, or 10 and 100, or 10 and 70, or 10 and 50. Formulations in accordance with certain of the preferred embodiments in various aspects of the disclosure provide compositions comprising a re-oxidized antigen-binding protein and a carrier, and further comprising one or more pharmaceutically acceptable salts; osmotic balancing agents (tonicity agents); anti-oxidants; antibiotics; antimycotics; bulking agents; lyoprotectants; anti-foaming agents; chelating agents; preservatives; colorants; analgesics; or additional pharmaceutical agents.

In some embodiments, the carrier is a solid, such as a powder in which a protein may be dispersed. In preferred embodiments in this regard, the carrier is a liquid, particularly a liquid in which the self-buffering protein is highly soluble, particularly at concentrations that provide the desired buffer capacity. Liquid carriers may be organic or non-organic. Preferably they are aqueous, most preferably they are largely or entirely comprised of pure water. In some embodiments, the carrier comprises a pharmaceutically acceptable buffer, e.g., acetate, succinate, citrate, histidine (imidazole), phosphate, Tris, or combinations thereof. The carrier may also comprises a biological buffer are biological buffers, such as those described in, among other texts: TEITZ TEXTBOOK OF CLINICAL CHEMISTRY, 3rd Ed., Burtis and Ashwood, eds., W.B. Saunders Company, Philadelphia, Pa. (1999), in particular in Tables 50-13 to 50-16, which are herein incorporated by reference in their entireties as to buffering agents and buffers; THE TOOLS OF BIOCHEMISTRY, Terrance G. Cooper, John Wiley & Sons, New York, N.Y. (1977), in particular Chapter 1, pages 1-35, which is herein incorporated by reference in its entirety, most particularly as to Tables 1-3, 1-4, and 1-5 and text relating thereto, and PROTEIN PURIFICATION PRINCIPLES AND PRACTICE, 3rd Ed., Robert K. Scopes, Springer-Verlag, New York, N.Y. (1994), in particular pages 160-164, especially therein Tables 6.4 and 6.5 and text relating thereto, Chapter 12, section 3, pages 324-333, especially therein Tables 12-4 and 12-5 and text relating thereto, and all of Appendix C: Buffers for Use in Protein Chemistry, which are herein incorporated by reference in their entireties. In some embodiments, the formulation is self-buffering, for example, as described in U.S. Patent Publication No. 20080311078, incorporated herein by reference.

Formulations in accordance with certain of the preferred embodiments in various aspects of the disclosure provide compositions comprising a re-oxidized antigen-binding protein and a carrier, in a solution that is hypotonic, isotonic, or hypertonic, preferably approximately isotonic, and may comprise one or more polyols including sugars, especially preferably any one or more of sorbitol, mannitol, sucrose, glucose, lactose, trehalose, propylene glycol, or glycerol. In some embodiments, formulations according to the disclosure further comprise one or more pharmaceutically acceptable surfactants, preferably one or more of polysorbate 20, polysorbate 80, other fatty acid esters of sorbitan, polyethoxylates, or poloxamer 188. Additional excipients can be used in the formulations according to the disclosure for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

In some embodiments, a formulation according to the disclosure comprises one or more salts, for example, to adjust the ionic strength and/or the isotonicity and/or the viscosity of the formulation and/or to improve the solubility and/or physical stability of the re-oxidized antigen-binding protein. Optionally, the salt concentration is less than 150 mM, for example, less than 125 mM, less than 100 mM, less than 75 mM, less than 50 mM, or less than 25 mM In some embodiments, a formulation according to the disclosure comprise one or more amino acids, for example, lysine, proline, serine, alanine, glycine, arginine, methionine, or combinations thereof, as, for example, a bulking agent, stabilizer, and/or antioxidant.

In some embodiments, a formulation according to the disclosure comprises one or more antioxidants, for example, one or more of a reducing agent, an oxygen/free-radical scavenger, or chelating agent, including, but not limited to, EDTA and glutathione. In some embodiments, the amount of EDTA is between 0.5 and 15 mM, such as 1 to 10 mM, 2 to 8 mM, 3 to 7, mM, 3 to 4 mM, 4 to 5 mM, or 5 to 6 mM. In some embodiments, the concentration of EDTA is 5 mM. In some embodiments, the EDTA inhibits thioredoxin or thioredoxin-like protein. In some embodiments, a formulation according to the disclosure comprises one or metal ions, including, but not limited to metals with a $^{+2}$ or higher oxidation state (such as $^{+3}$ or $^{+4}$), such as $Mg^{+2}$, $Mn^{+2}$, $Ca^{+2}$, $Zn^{+2}$, $Cu^{+2}$, $Cd^{+2}$, $Co^{+2}$, $Sr^{+2}$, or $Al^{+3}$. In some embodiments, the concentration of metal is between 1 to 900 ppm, such as 10 to 800 ppm, 100 to 700 ppm, 10 to 100 ppm, 100 to 200 ppm, 200 to 300 ppm, 300 to 400 ppm, 400 to 500 ppm, 500 to 600 ppm, or 600 to 700 ppm.

Optionally, a formulation according to the disclosure comprises a preservative, to inhibit microbial growth and maintain sterility. Examples of suitable preservatives include, but are not limited to, benzyl alcohol, phenol, m-cresol, butyl alcohol, parabens, resorcinol, catechol, cyclohexanol, 3-pentanol, quaternary ammonium salts, and combinations thereof.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety.

Formulations in accordance with the disclosure, in various embodiments, may be administered by a variety of suitable routes, well-known to those skilled in the art of administering therapeutics to a subject. Such routes in a variety of embodiments include but are not limited to administration of the compositions orally, ocularly, mucosally, topically, rectally, pulmonarily, such as by inhalation spray, and epicutaneously. The following parenteral routes of administration also are useful in various embodiments of the invention: administration by intravenous, intraarterial, intracardiac, intraspinal, intrathecal, intraosseous, intraarticular, intrasynovial, intracutaneous, intradermal, subcutaneous, peritoneal, and/or intramuscular injection. In some embodiments intravenous, intraarterial, intracutaneous, intradermal, subcutaneous and/or intramuscular injection are used. In some embodiments. subcutaneous, and/or intramuscular injection are used.

The present disclosure will be more readily understood by reference to the following Examples, which are provided by way of illustration and are not intended to be limiting.

EXAMPLES

The present invention is additionally described by way of the following illustrative, non-limiting Examples.

Example 1

Reduction of Antibody Molecules During Antibody Production

Production and purification of recombinant antibody molecules from host cells grown in a bioreactor can result in the partial reduction of some of the antibody molecules, thereby reducing the therapeutic efficacy of the molecules. The partial reduction of the antibody molecules can begin in the bioreactor and continue throughout the production and purification process, even if aerating steps are added in an attempt to re-oxidize the reduced antibody molecules. The following Examples investigate the reduction of antibody molecules over the course of the production and purification process and the effects of one or more depth filtration steps on enhancing re-oxidation of the antibody molecules and reducing the percentage of reduced antibody molecules in an aqueous solution.

Cell culture fluid comprising recombinant antibody molecules was harvested and clarified using cross-flow microfiltration. The harvested cell culture fluid (HCCF) was sparged with air and/or chilled and optionally subjected to one or more freeze/thaw cycles. Protein A chromatography was carried out in accordance with the resin manufacturer's instructions to form a Protein A pool. The amount of partially reduced antibody molecules in the HCCF and Protein A pool were analyzed using nrCE-SDS to determine the percentage of pre-peak species corresponding to partially reduced antibody molecules. Partially reduced antibodies were present in the HCCF, but the percentage of reduced antibodies was significantly higher in the Protein A pool compared to the HCCF.

In a particular example, host cells producing an anti-CD20 IgG1 antibody with a kappa light chain having a heavy chain variable region of SEQ ID NO: 1 and a light chain variable region of SEQ ID NO: 2 (Antibody A) were cultured in a bioreactor for up to 15 days. The cell culture fluid comprising the antibody was harvested and clarified using cross-flow microfiltration. The harvested cell culture fluid (HCCF) was then sparged with air and/or chilled to maintain 80±15% dissolved oxygen and/or a temperature of 2° C. to 8° C. The sparged/chilled HCCF was brought to room temperature prior to being subjected to Protein A chromatography using an AKTA Explorer and MabSelect SuRE resin (GE Healthcare Life Sciences, Pittsburgh, Pa.) in accordance with the manufacturer's instructions to form a Protein A pool. The amount of partially reduced antibody molecules in the HCCF and Protein A pool were analyzed using nrCE-SDS to determine the percentage of pre-peak species corresponding to partially reduced antibody molecules (FIG. 1). The reduction of antibody molecules began in the bioreactor. Despite a decrease in the percentage of partially reduced antibodies after air sparging and chilling the cell culture fluid, reduction of the disulfide bonds continued post-harvest, and the percentage of pre-peak species was significantly higher in the Protein A pool compared to the harvested cell culture fluid. Therefore, the controlled oxygen and temperature conditions, i.e., air sparging and chilling of the harvested cell culture fluid, were not sufficient to prevent the partial reduction of the antibody molecules and did not sufficiently enhance re-oxidation.

Example 2

Figure 2:
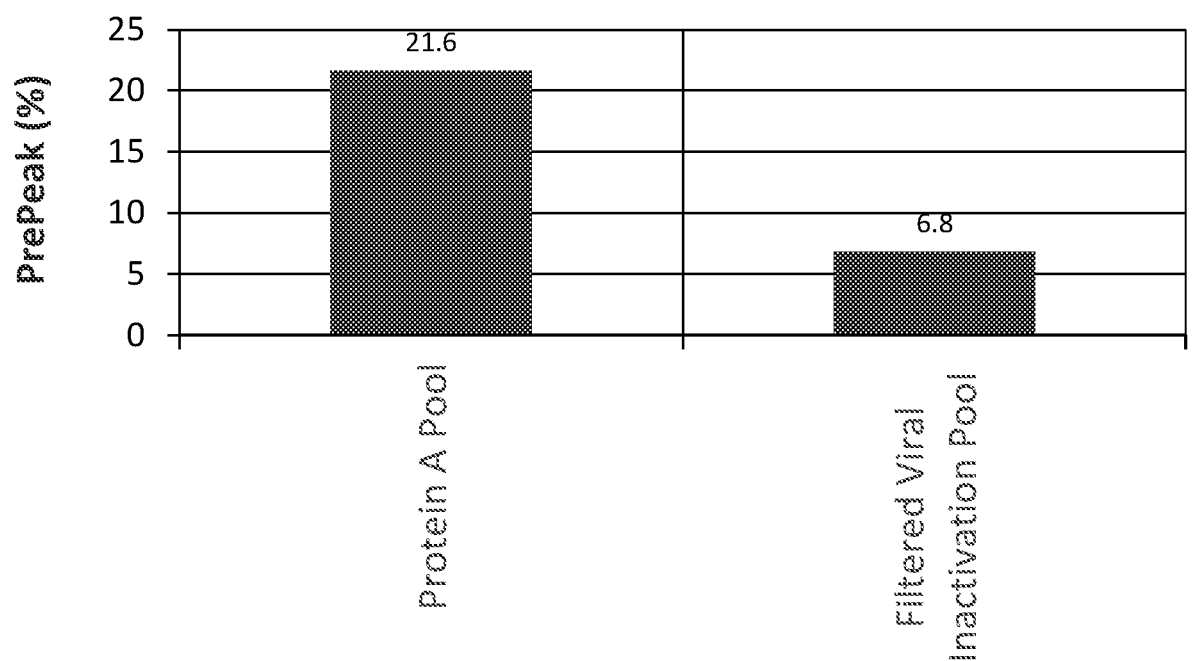
FIG. 2 depicts the level of partial antibody reduction as the percentage of pre-peak species in (a) the Protein A Pool, before passing through the charged depth filter, and (b) filtered viral inactivation pool, after passing through the charged depth filter.

Enhanced Re-Oxidation of Partially Reduced Antibody Molecules Following Charged Depth Filtration An aqueous antibody solution comprising Antibody A was subjected to Protein A chromatography as described above and then a viral inactivation step comprising reducing the pH of the Protein A pool to about pH 3.6 for 1 hour and then adjusting to pH 5 was performed to form a neutralized viral inactivation pool (nVIP). The nVIP was subjected to charged depth filtration using a MILLISTAK+ A1HC charged depth filter system (EMD Millipore) followed by sterile filtration using a Millipore EXPRESS SHC hydrophilic filter in accordance with the manufacturer's instructions to form a filtered viral inactivation pool (FVIP). Filtration was performed using a normal flow filtration system (PendoTECH, Princeton, N.J.) with the filter connected to a pressure sensor to monitor and control the pressure limit. The flowrate and pressure were maintained at ≤ about 200 LMH and ≤ about 50 psi, respectively. The filter was first flushed with deionized water for about 100 L/m², followed by a equilibration phase with 30 mM acetate buffer, pH 5.0, for ≥ about 50 L/m² prior to loading the solution to be filtered in the range of about 50 L/m² to about 800 L/m². At the end, the filter was flushed with about 20 L/m² of the equilibration buffer. The level of partial antibody reduction as the percentage of pre-peak species measured by nrCE-SDS in the Protein A pool and the FVIP was determined (FIG. 2). Following contact with the charged depth filter, the amount of partially reduced antibody in the Protein A pool was significantly decreased, with a greater than 3-fold decrease in the % pre-peaks observed. All of the Protein A pool product mass was recovered following filtration using the charged depth filter, demonstrating that the decrease in % pre-peak species was due to re-oxidation of partially reduced antibody following contact with the charged depth filter according to the disclosure and not loss of antibody molecules. The presence of thioredoxin and thioredoxin reductase was determined using mass spectrophotometry. Thioredoxin like proteins were present in the Protein A Pool, but the charged depth filtrate was free of both thioredoxin and thioredoxin reductase.

Figure 3A:
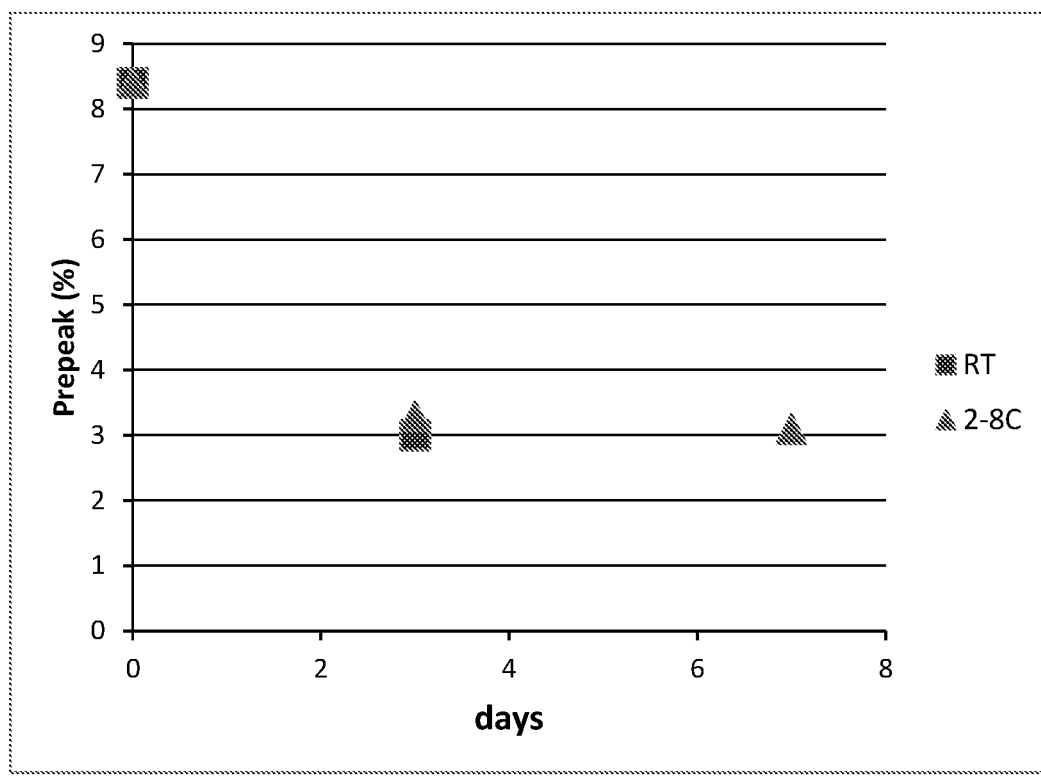
FIG. 3A depicts the level of partial antibody reduction as the percentage of pre-peak species in a charged depth filtered Protein A pool for up to 8 days post-filtration at room temperature or 2° C. to 8° C.
Figure 3B:
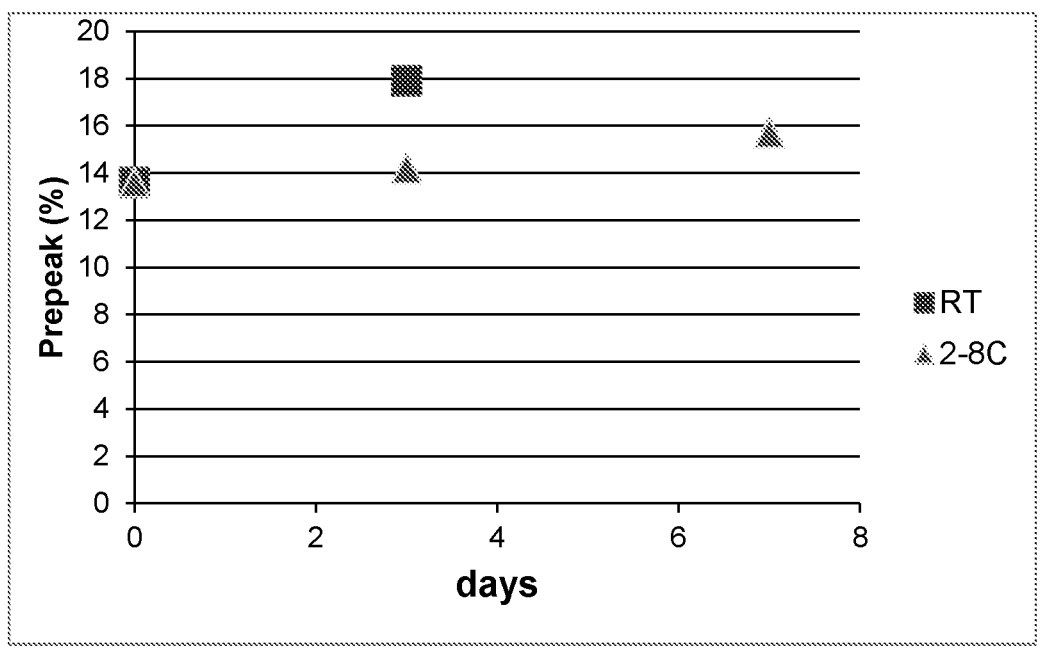
FIG. 3B depicts the level of partial antibody reduction as the percentage of pre-peak species in a non-charged depth filtered Protein A pool for up to 8 days post-filtration at room temperature or 2° C. to 8° C.

To further evaluate the enhanced re-oxidation of antibody molecules, a Protein A pool was prepared and contacted with a charged depth filter to form a FVIP as described above or not filtered further and then held at room temperature or a temperature between 2° C. and 8° C., for up to 8 days. The level of partial antibody reduction as the percentage of pre-peak species measured by nrCE-SDS in the FVIP (FIG. 3A) or non-charged depth filtered Protein A pool (FIG. 3B) was determined. The percentage of pre-peak species in the FVIP continued to decrease following contact with the charged depth filter, and the re-oxidation was enhanced at both room temperature and between 2° C. and 8° C. The amount of partially reduced antibody molecules in the FVIP decreased almost three-fold and reached a steady state level in three days or less. In contrast, the percentage of pre-peak species in the non-filtered Protein A pool continued to increase over time at both temperatures, indicating further reduction of the antibody molecules, with faster reduction kinetics at room temperature compared to when chilled.

Figure 4A:
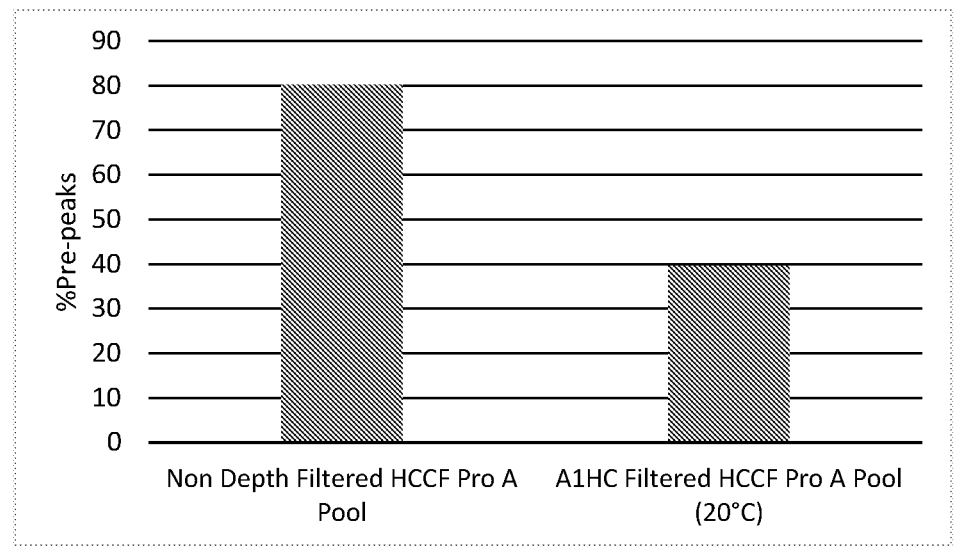
FIG. 4A depicts the level of partial antibody reduction as the percentage of pre-peak species in HCCF subjected to charged depth filtration or no filtration, followed by Protein A chromatography.
Figure 4B:
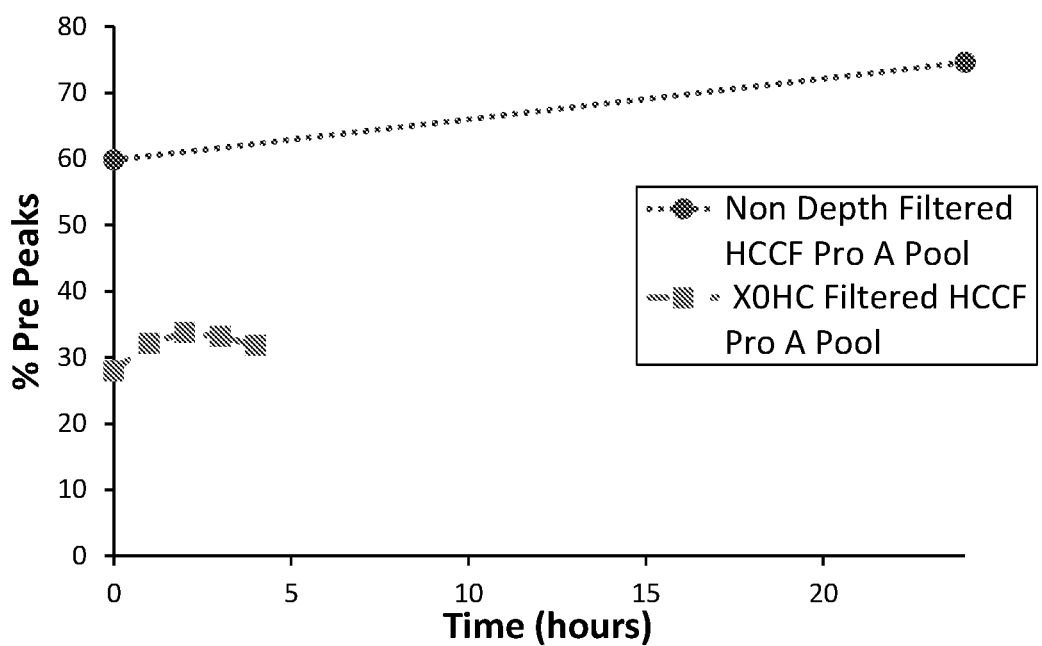
FIG. 4B depicts the level of partial antibody reduction as the percentage of pre-peak species in HCCF subjected to charged depth filtration or no filtration, followed by Protein A chromatography, for up to 24 hours post-filtration.

The charged depth filtration was also effective in enhancing re-oxidation of antibody molecules when performed prior to Protein A chromatography. HCCF was subjected to either charged depth filtration using a MILLISTAK+ X0HC depth filter system (EMD Millipore) in accordance with the manufacturer's instructions and at a throughput of 350 L/m$^2$ or no filtration and then subjected to Protein A chromatography to form a Protein A pool. The level of partial antibody reduction as the percentage of pre-peak species measured by nrCE-SDS in the charged depth filtered Protein A pool or non-charged depth filtered Protein A pool was determined (FIG. 4A and FIG. 4B). There was an approximately 2-fold (50%) reduction in the percentage of pre-peak species observed in the Protein A pool using the charged depth filtrate as the load material, compared to the non-filtered control (FIG. 4A). In addition, the Protein A pool from the charged depth filtrate was more stable, with the percentage of pre-peak species remaining relatively constant, compared to the non-filtered control, whose levels of partially reduced antibody molecules continued to increase following the Protein A chromatography (FIG. 4B).

The results demonstrated that contacting an aqueous solution comprising antibody molecules with a charged depth filter according to the disclosure effectively enhanced re-oxidation of the antibody molecules, resulting in a decreased amount of partially reduced antibody molecules.

Example 3

Comparison of Filtration Methods on Re-Oxidation of Antibody Molecules

Figure 5A:
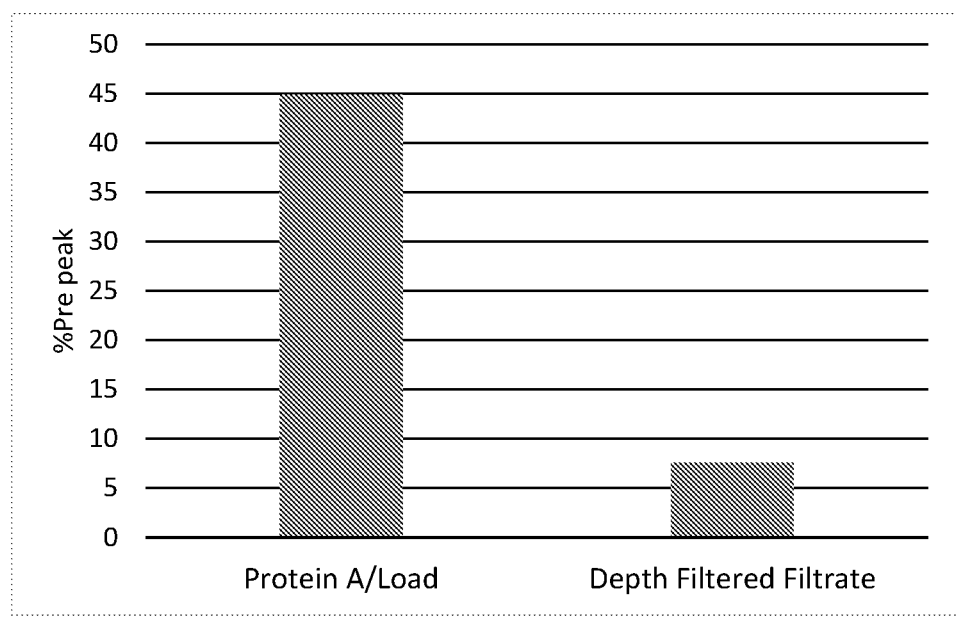
FIG. 5A depicts the level of partial antibody reduction as the percentage of pre-peak species in a Protein A pool as load compared to the depth filtered filtrate.
Figure 5B:
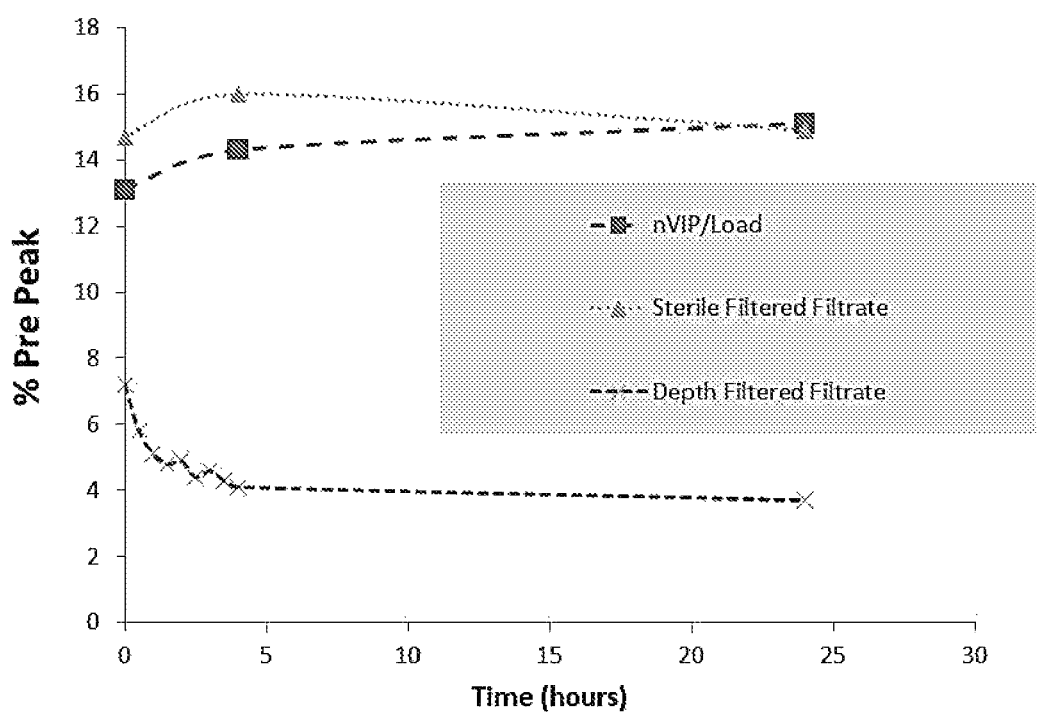
FIG. 5B depicts the level of partial antibody reduction as the percentage of pre-peak species in a neutralized viral inactivation pool (a) before filtration (nVIP/Load), (b) following sterile membrane filtration and (c) following charged depth filtration, for up to 24 hours post-filtration.

An nVIP was produced as described in Example 2 and subjected to either charged depth filtration using a MILLISTAK+ A1HC depth filter system or sterile membrane filtration using a Millipore EXPRESS SHC hydrophilic filter at a throughput of 350 L/m$^2$. The level of partial antibody reduction as the percentage of pre-peak species measured by nrCE-SDS in the nVIP loaded into the filter system and following filtration was determined (FIG. 5A and FIG. 5B). Charged depth filtration was shown to facilitate re-oxidation of even highly reduced material achieving a decrease in the percentage of pre-peak species from 45% in the load to less than 10% in the depth filtered filtrate (FIG. 5A). The percentage of pre-peak species in the nVIP and sterile-filtered filtrate were comparable, indicating that aeration due to filtration alone did not facilitate re-oxidation of the antibody molecules. However, there was a more than two-fold decrease in % pre-peaks observed in the charged depth filtered filtrate, compared to the sterile filtered filtrate immediate following filtration (t=0). Additionally, the percentage of pre-peak species in the charged depth filtered filtrate continued to decrease over the first four hours post-filtration hold and achieved steady state level by 4 hours that was more than three-fold lower than the percentage of pre-peak species in the nVIP or sterile filtered filtrate. The use of a charged depth filter specifically, and not the act of filtering, thus facilitated the re-oxidization of partially reduced antibodies.

Example 4

Figure 6:
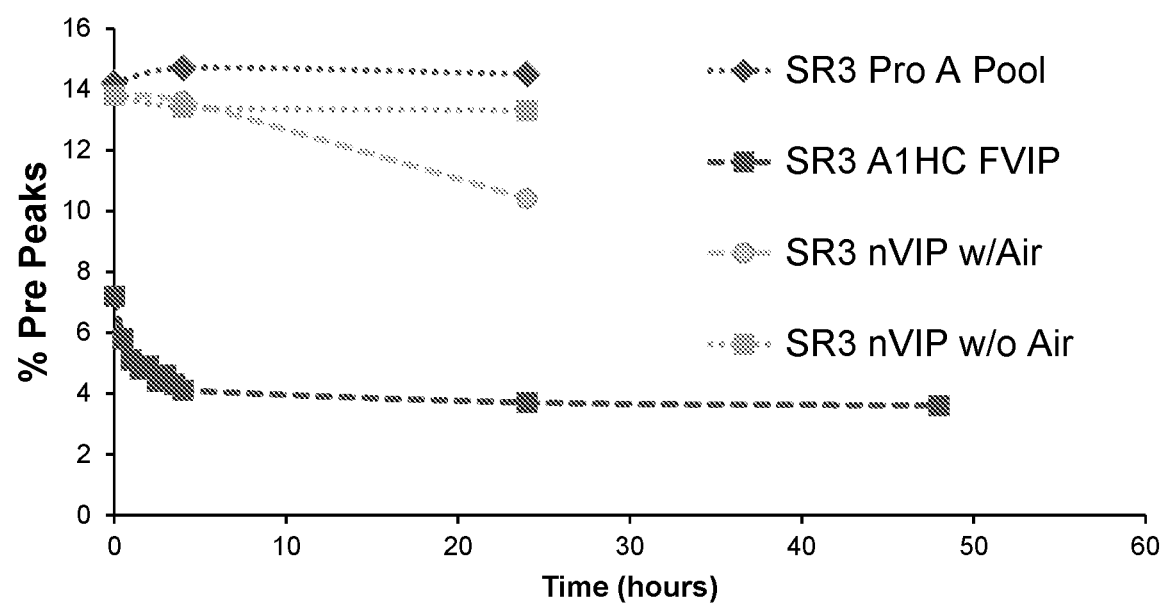
FIG. 6 depicts the level of partial antibody reduction as the percentage of pre-peak species in a non-charged depth filtered Protein A pool, a charged depth filtered FVIP pool, a nVIP Pool oxygenated with air and a nVIP pool without air, for up to 50 hours post-filtration.

Effect of Charged Depth Filtration and Oxygenation on Re-Oxidation of Antibody Molecules An aqueous solution comprising Antibody A was subject to Protein A chromatography followed by (a) a viral inactivation step and then charged depth filtration using a MILLISTAK+ A1HC charged depth filter system to form a FVIP; (b) a viral inactivation step to form a nVIP followed by air sparging to 100% dissolved oxygen; or (c) viral inactivation only to form a nVIP followed up a hold step for up to 50 hours, or (d) the hold step only as a control. The level of partial antibody reduction as the percentage of pre-peak species measured by nrCE-SDS in the Protein A Pool, FVIP, nVIP oxygenated with air and nVIP without air was compared (FIG. 6). The starting percentage of pre-peak species was comparable among the Protein A pool and the nVIPs, regardless of whether the nVIP was oxygenated with air. In contrast, the amount of reduced antibody molecules following charged depth filtration in the FVIP was approximately two-fold lower. The percentage of pre-peak species in the FVIP continued to decrease during the hold, reaching a steady state level more than three-fold lower than the Protein A pool or non-oxygenated nVIP and more than two-fold lower than the oxygenated nVIP. The presence of 100% saturated oxygen had minimal impact, therefore, on re-oxidization of the antibody molecules and was much less effective than the charged depth filtration on decreasing the amount of partially reduced antibody molecules.

Example 5

Effect of Charged Depth Filter Throughput on Re-Oxidation of Antibody Molecules

Figure 7A:
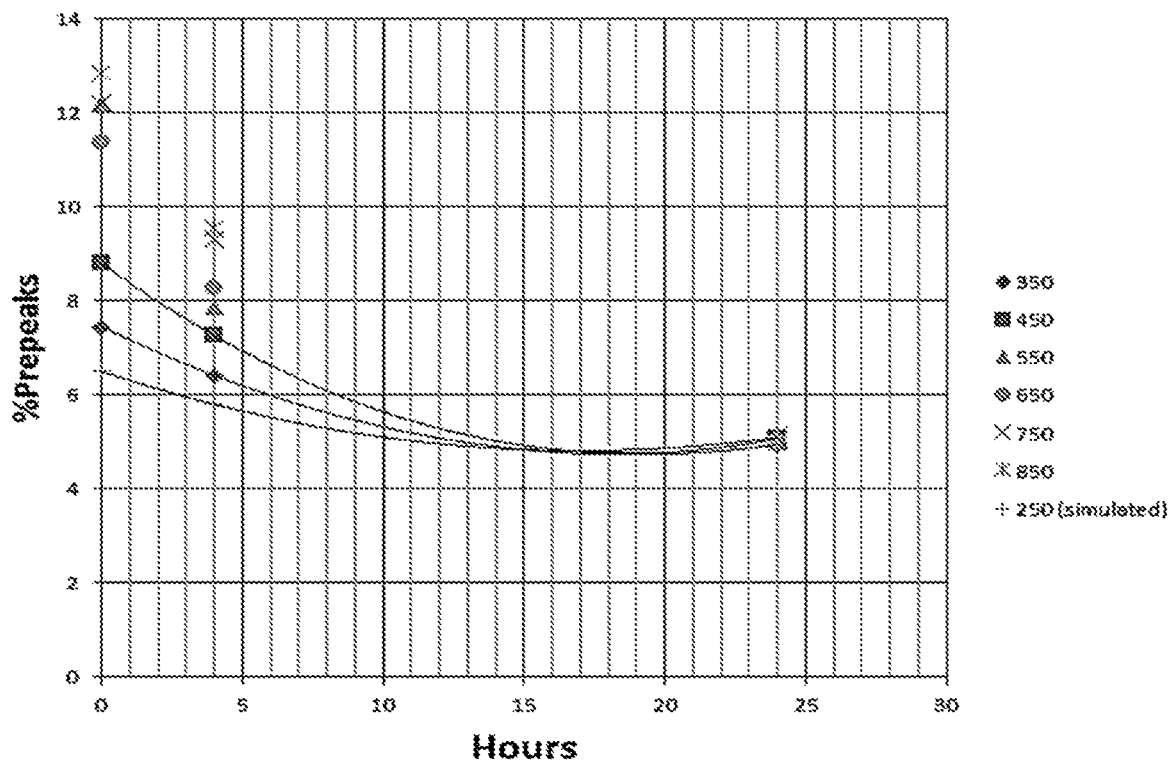
FIG. 7A depicts the level of partial antibody reduction as the percentage of pre-peak species following charged depth filtration at a throughput of 250 L/m$^2$ (simulated) and 350 L/m$^2$ to 850 L/m$^2$ (experimental) for up to 24 hours post-filtration.
Figure 7B:
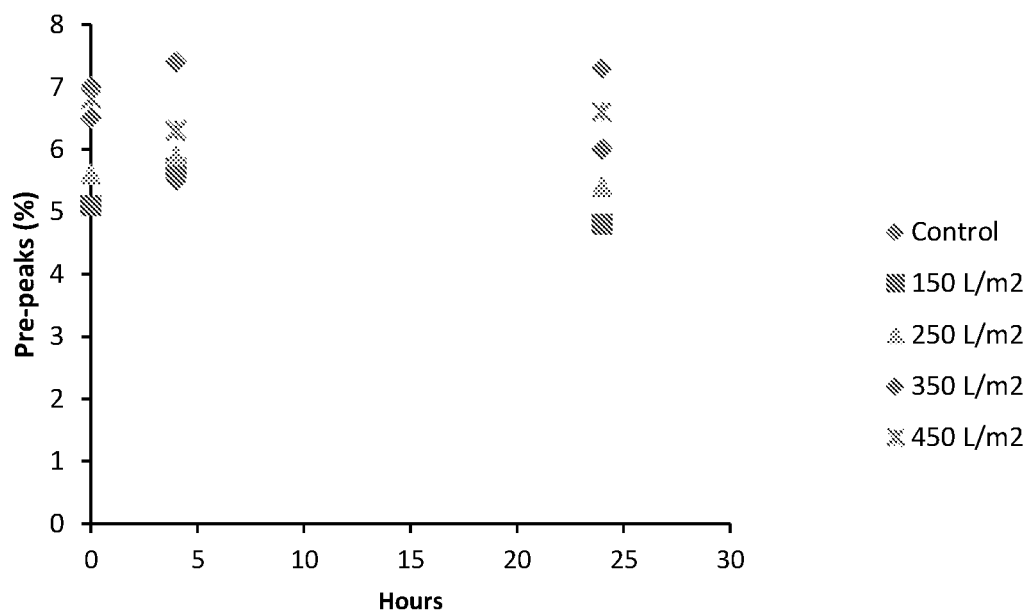
FIG. 7B depicts the level of partial antibody reduction as the percentage of pre-peak species following charged depth filtration at a throughput of 150 L/m$^2$ to 450 L/m$^2$ for up to 24 hours post-filtration.

The effect of throughput, i.e., the total amount of aqueous solution contacted with a charged depth filter per square meter of filter, on re-oxidation of partially reduced antibodies was evaluated. Aqueous solutions comprising Antibody A were subjected to charged depth filtration using a MILLISTAK+ A1HC filter as described above at a throughput of 350 L/m$^2$ to 850 L/m$^2$, and the level of partial antibody reduction as the percentage of pre-peak species was measured by nrCE-SDS for up to 24 hours post-filtration (FIG. 7A). As throughput increased, the kinetics of re-oxidation of the antibody molecules during the first hours following filtration slowed; however, by 24 hours post-filtration, all throughputs tested achieved the same steady state percentage of pre-peak species, demonstrating broad applicability of the methods of the disclosure to industrial purposes. A similar experiment conducted using a Cuno Zeta+ SP90 charged depth filter at a throughput of 150 L/m$^2$ to 450 L/m$^2$ also achieved enhanced re-oxidation and a decrease in the level of partial antibody reduction at all throughputs tested (FIG. 7B).

Example 6

Effect of CEX Chromatography on Re-Oxidation of Antibody Molecules

Figure 8A:
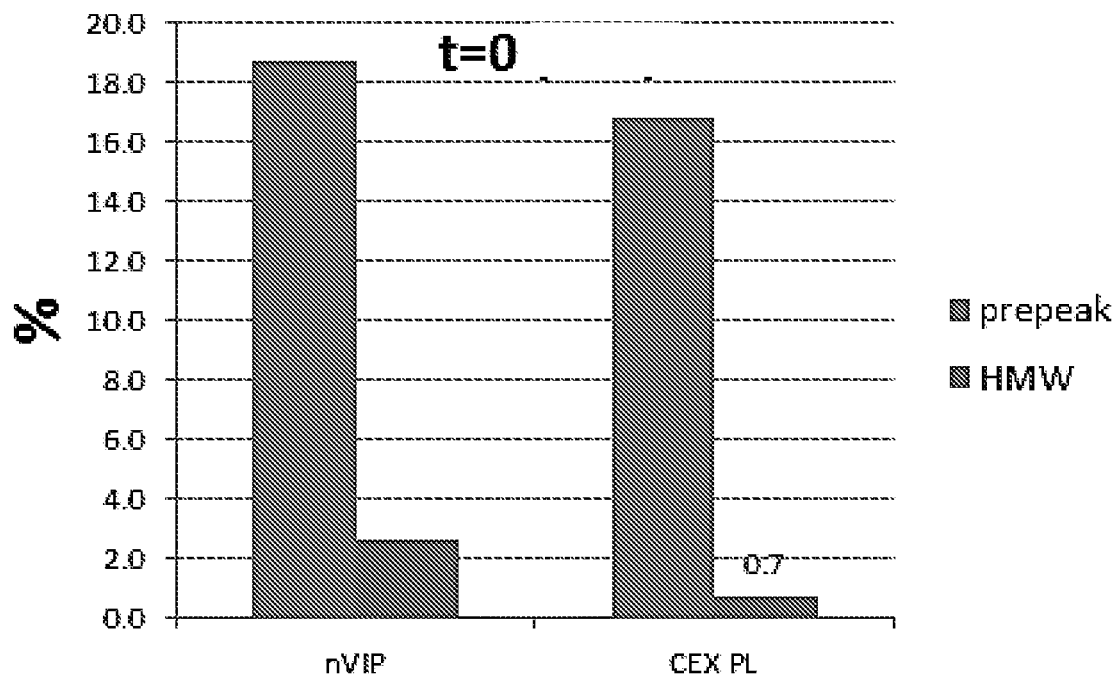
FIG. 8A depicts the level of partial antibody reduction as the percentage of pre-peak species (prepeak) and high molecular weight species (HMW) before (nVIP) and after cation exchange chromatography (CEX PL) without charged depth filtration.
Figure 8B:
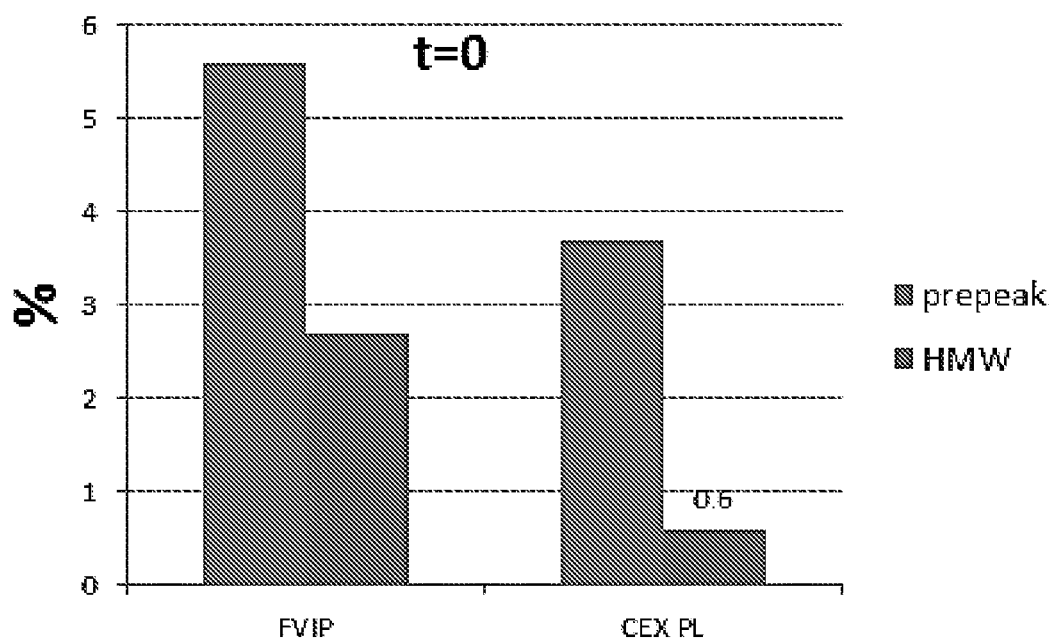
FIG. 8B depicts the level of partial antibody reduction as the percentage of pre-peak species (prepeak) and high molecular weight species (HMW) following charged depth filtration only (FVIP) or charged depth filtration followed by cation exchange chromatography (CEX PL) immediately post-processing (t=0).
Figure 8C:
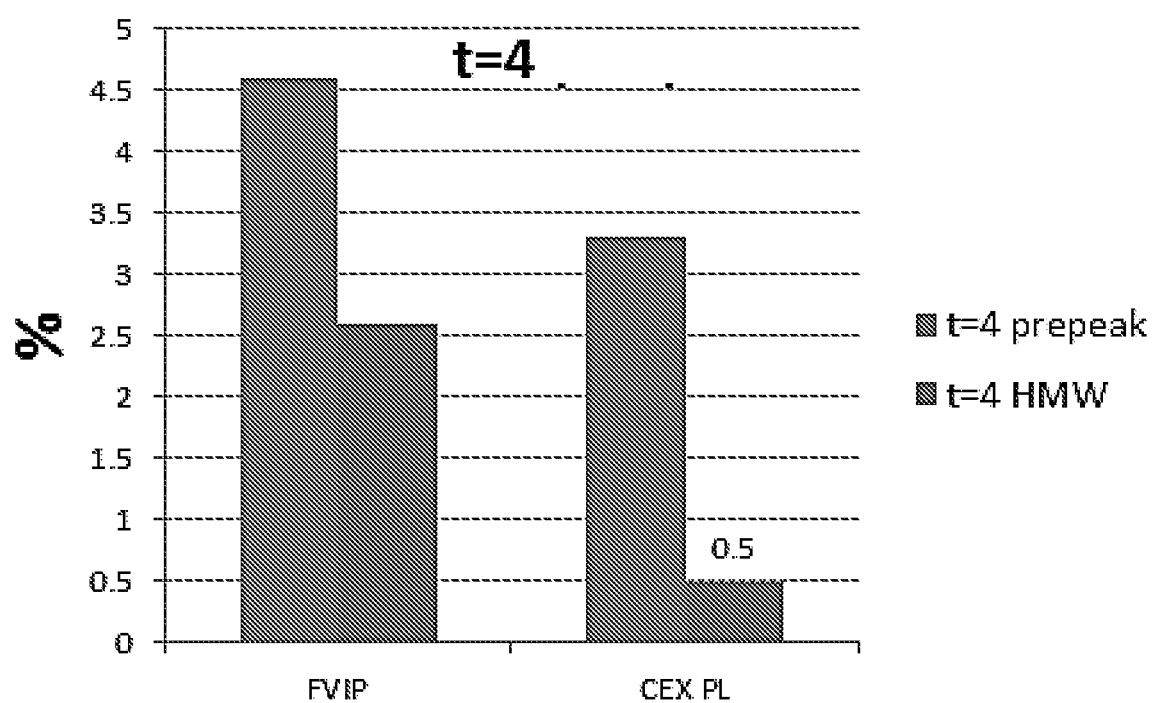
FIG. 8C depicts the level of partial antibody reduction as the percentage of pre-peak species (prepeak) and high molecular weight species (HMW) following charged depth filtration only (FVIP) or charged depth filtration followed by cation exchange chromatography (CEX PL) at four hours (t=4) post-processing.

An aqueous solution comprising Antibody A was subjected to Protein A chromatography and then a viral inactivation step to form a nVIP. The nVIP was subjected to (a) CEX chromatography only at 50 g/L using a FRACTOGEL SO3 resin (EMD Millipore) to form a CEX pool; (b) charged depth filtration only using a MILLISTAK+ A1HC depth filter system to form a FVIP, or (c) charged depth filtration to form a FVIP, followed by CEX chromatography, as described in (a) and (b), to form a CEX pool. The CEX step was designed to resolve high molecular weight (HMW) species in a bind and elute mode. Partial antibody molecules can dimerize on the resin via free thiol and elute out as HMW species. The level of partial antibody reduction as the percentage of pre-peak species was measured by nrCE-SDS before and after CEX chromatography of the nVIP (FIG. 8A) and immediately following CEX chromatography of the charged depth filtered FVIP (FIG. 8B) as well as 4 hours post-CEX chromatography of the charged depth filtered FVIP (FIG. 8C). The percentage of HMW species was also determined as a measure of partial antibody molecules. The percentage of reduced pre-peak species in the non-charged depth filtered nVIP before and after CEX chromatography were comparable (FIG. 8A). The level of reduced antibody in the FVIP was more than three-fold lower than in the nVIP following charged depth filtration. The percentage of pre-peak species in the charged depth filtered FVIP was further decreased by more than 1.5-fold immediately following CEX chromatography (FIG. 8B) and was comparable at 0 and 4 hours post-CEX chromatography (FIGS. 8B and 8C). Additionally, the percentage of HMW species in the charged depth filtered FVIP decreased following CEX chromatography, confirming a decrease in partial antibody molecules. The results indicated that re-oxidation of the antibody species following charged depth filtration continued on the CEX column and reached steady state.

Example 7

Figure 9A:
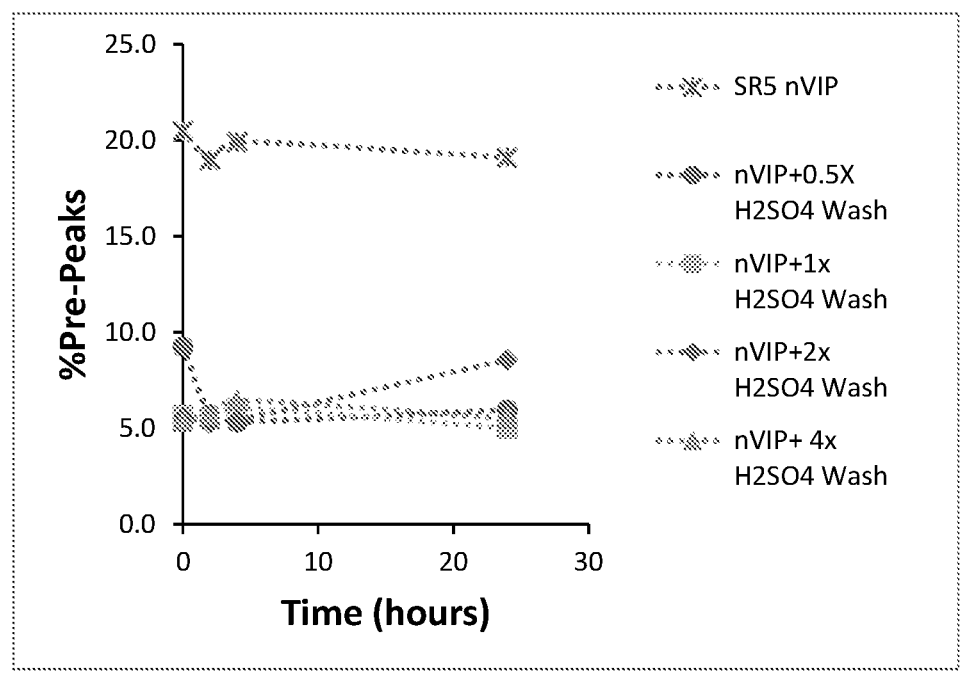
FIG. 9A depicts the level of partial antibody reduction as the percentage of pre-peak species in nVIP samples spiked with 0.5× to 4× of $H_2SO_4$ wash obtained by recirculating $H_2SO_4$ through a charged depth filter for 2 hours or unspiked nVIP.
Figure 9B:
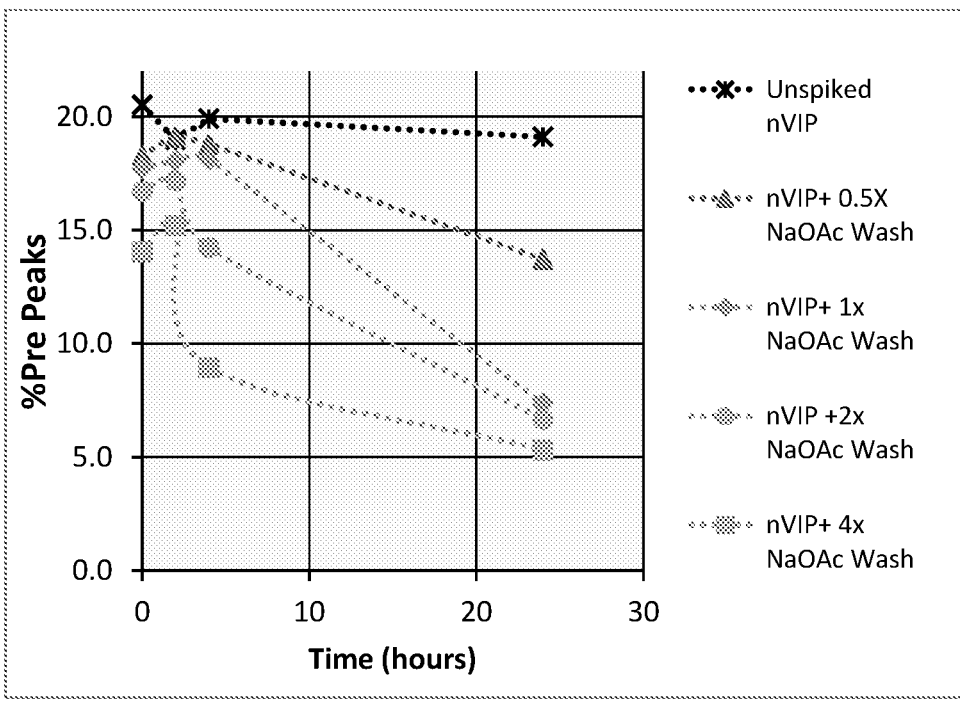
FIG. 9B depicts the level of partial antibody reduction as the percentage of pre-peak species in nVIP samples spiked with 0.5× to 4× of acetate (NaOAc) wash obtained by recirculating NaOAc through a charged depth filter for 2 hours, or unspiked nVIP.

Effect of Charged Depth Filter Components on Re-Oxidation of Antibody Molecules A charged depth filter was flushed with deionized water for 100 L/m², followed by a 2-hour recirculation phase with a 0.1 M $H_2SO_4$ solution to strip the filter and remove bound metals, or with a 100 mM acetate solution, pH 5.0, as a control. An aqueous solution comprising Antibody A was subjected to Protein A chromatography and then a viral inactivation step followed by a neutralization step to form a nVIP. After the 2-hour recirculation, the acetate and sulfuric solutions were spiked into nVIP samples at different volume ratios of 0.5, 1, 2 and 4 parts of buffer to 1 part of nVIP. The sulfuric solution contained bound metals and other material stripped from the charged depth filter. For example, the sulfuric solution contained about 1500 parts per billion (ppb) $Cu^{2+}$, while the acetate solution compared less than 5 ppb $Cu^{2+}$. The level of partial antibody reduction as the percentage of pre-peak species in the spiked samples was measured by nrCE-SDS at 0, 2, 4 and 24 hours post-spike. As expected, unspiked nVIP exhibited no re-oxidation of the antibody molecules. In contrast, the percentage of pre-peak species in the nVIP spiked with the sulfuric solution were significantly lower (FIG. 9A). The percentage of pre-peak species in the nVIP spiked with the sulfuric acid solution at a concentration of 1× or above reached steady state at t=0, indicated that contacting the nVIP with the components stripped from the charged depth filter efficiently enhanced re-oxidation. Spiking the nVIP with the acetate solution was not as efficient in facilitating re-oxidization of the antibody molecules as the sulfuric solution or direct contact of antibody with the depth filter (FIG. 9B). The percentage of pre-peak species in the nVIP spiked with the acetate solution was higher at t=0 compared to the sulfuric solution-spiked nVIP, and steady state was still not achieved after a 24-hour hold. The results demonstrated that components obtained from the charged depth filter were able to efficiently enhance re-oxidation of partially reduced antibody molecules.

Example 8

Processes for Re-Oxidizing Reduced Antibody Molecules

Table 1 describes Processes A through N for preparing aqueous solutions comprising re-oxidized antibody molecules.

TABLE 1

| Process Steps | Process | | | | | | | | | | | | | |
|---|---|---|---|---|---|---|---|---|---|---|---|---|---|---|
| | A | B | C | D | E | F | G | H | I | J | K | L | M | N |
| Depth Filtration | X | | X | X | X | X | | | | | | | | X |
| Protein A Chromatography | X | X | X | X | X | X | X | X | X | X | X | X | X | X |
| Depth Filtration | X | X | | X | X | X | | | X | | X | | | |
| Viral Inactivation | X | X | X | X | X | X | X | X | X | X | X | X | X | X |
| Depth Filtration | X | X | X | | X | X | X | X | X | X | | X | | X |
| Cation Exchange Chromatography | X | X | X | X | X | X | X | X | X | X | X | X | X | X |
| Depth Filtration | X | X | X | X | | X | | X | | X | X | | X | X |
| Additional Chromatography (e.g., STIC PA, HIC, MMC) | X | X | X | X | X | X | X | X | X | X | X | X | X | X |
| Depth Filtration | X | X | X | X | X | | | | | X | | | X | X |

First, aqueous solutions comprising reduced antigen-binding protein molecules, e.g., HCCF, are obtained without sparging the cell culture fluid with air. In Process A, for example, the aqueous solution is subjected to a charged depth filtration step to form a first filtrate, and the first filtrate is subjected to a Protein A chromatography step to form a first eluate. The first eluate is subjected to a charged depth filtration step to form a second filtrate, and the second filtrate is subjected to a low pH viral inactivation step to form a virally inactivated second filtrate. The virally inactivated second filtrate is subjected to a charged depth filtration step to form a third filtrate. The third filtrate is subjected to a cation exchange chromatography step to form a second eluate, followed by a charged depth filtration step to form a fourth filtrate. The fourth filtrate is subjected to one or more additional chromatography steps, for example, STIC PA, HIC, and/or MMC, to form a third (or fourth or fifth) eluate, followed by a charged depth filtration step to form a fifth filtrate.

In another example, for Process B, the aqueous solution is subjected to a Protein A chromatography step to form a first eluate. The first eluate is subjected to a charged depth filtration step to form a first filtrate, and the first filtrate is subjected to a low pH viral inactivation step to form a virally inactivated first filtrate. The virally inactivated first filtrate is subjected to a charged depth filtration step to form a second filtrate. The second filtrate is subjected to a cation exchange chromatography step to form a second eluate, followed by a charged depth filtration step to form a third filtrate. The third filtrate is subjected to one or more additional chromatography steps, for example, STIC PA, HIC, and/or MMC, to form a third (or fourth or fifth) eluate, followed by a charged depth filtration step to form a fourth filtrate.

In any of Processes A through N, the Process optionally further includes additional, subsequent purification steps, for example, one or more of ultrafiltration, diafiltration, and viral filtration steps, to achieve an aqueous solution comprising re-oxidized antibody molecules. In any of Processes A through N, the aqueous solution comprising re-oxidized antibody molecules achieved using the Process has a decreased percentage of reduced antigen-binding protein molecules, compared to the percentage of reduced antigen-binding protein molecules observed prior to the start of the Process.

The foregoing Examples demonstrate that contacting an aqueous solution comprising antigen-binding protein molecules with a charged depth filter according to the disclosure effectively enhances re-oxidation of partially reduced antigen-binding protein molecules, thereby restoring the structural integrity and related biological and therapeutic function of the antibodies.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A method of producing an aqueous formulation of an antigen-binding protein comprising
   (a) contacting an aqueous solution comprising antigen-binding protein molecules with a charged depth filter to form a filtrate, and
   (b) incubating the filtrate for at least four hours, wherein the percentage of reduced antigen-binding protein molecules in the filtrate after the incubating step is decreased by at least 20% when compared to the percentage of reduced antigen-binding protein molecules observed in the aqueous solution prior to the contacting step.

2. A method of enhancing re-oxidization of an antigen-binding protein comprising
   (a) contacting an aqueous solution comprising antigen-binding protein molecules with a charged depth filter to form a filtrate; and
   (b) incubating the filtrate for at least four hours, wherein the re-oxidation of the antigen-binding protein molecules in the filtrate is increased at least two-fold after the contacting step when compared to a level of re-oxidized antigen-binding molecules in the aqueous solution prior to the contacting step.

3. The method according to claim 1, wherein step (a) or step (b) is followed by subjecting the solution of antigen-binding protein molecules to Protein A chromatography.

4. The method according to claim 1, wherein step (a) is preceded by subjecting the solution of antigen-binding protein molecules to Protein A chromatography.

5. The method according to claim 1, further comprising a step of inactivating one or more viruses in said solution of antigen-binding protein molecules.

6. The method according to claim 1, wherein the amount of reduced disulfide bonds in the antigen-binding protein molecules is decreased by at least 15% following the charged depth filtration when compared to an amount of reduced disulfide bonds in the antigen-binding protein molecules in the aqueous solution before the contacting step and/or wherein the percentage of reduced antigen-binding protein molecules continues to decrease for at least 1 hours, at least 2 hours, at least 3 hours, or at least 4 hours following step (a).

7. The method according to claim 6, wherein the amount of reduced disulfide bonds in the antigen-binding protein molecules is decreased by at least 20% following the charged depth filtration when compared to an amount of reduced disulfide bonds in the antigen-binding protein molecules in the aqueous solution before the contacting step and/or wherein the percentage of reduced antigen-binding protein molecules continues to decrease for at least 1 hours, at least 2 hours, at least 3 hours, or at least 4 hours following step (a).

8. The method of claim 7, wherein the antigen-binding protein is an IgG antibody.

9. The method according to claim 8, wherein the antibody is an IgG1 antibody with a Kappa light chain, or an IgG1 antibody with a Lambda light chain.

10. The method according to claim 1, wherein the contacting occurs at room temperature or at a temperature of 2 degrees to 8 degrees Celsius.

11. The method according to claim 1, further comprising a step of sparging air or oxygen through the solution of antigen-binding protein molecules.

12. The method according to claim 1, further comprising contacting the solution of antigen-binding protein molecules with a positive ion selected from the group consisting of sodium, calcium, magnesium, mercury, molybdenum, chromium, cadmium, aluminum, potassium, cobalt, iron, manganese, titanium, zinc, nickel, copper, and combinations thereof.

13. The method according to claim 1, wherein the solution of antigen-binding protein molecules is contacted with more than one charged depth filter.

14. The method according to claim 1, wherein the charged depth filter comprises a diatomaceous earth layer.

15. The method according to claim 14, wherein the charged depth filter further comprises a cellulose layer and an inorganic layer.

16. The method according to claim 15, wherein the inorganic layer comprises a polyamine resin.

17. The method according to claim 1, wherein the charged depth filter comprises a positively charged ion selected from the group consisting of sodium, calcium, magnesium, mercury, molybdenum, chromium, cadmium, aluminum, potassium, cobalt, iron, manganese, titanium, zinc, nickel, copper, and combinations thereof.

18. The method according to claim 1, wherein the contacting occurs at a throughput of between 250 L/m$^2$ and 850 L/m$^2$.

19. The method according to claim 1, wherein the antigen-binding protein is an IgG antibody.

20. The method according to claim 1, wherein the antigen-binding protein is an IgG1 antibody with a Kappa light chain, or an IgG1 antibody with a Lambda light chain.

21. The method according to claim 1, wherein the antigen-binding protein binds an antigen selected from the group consisting of RANKL, tumor necrosis factor alpha, epidermal growth factor receptor, CD20, calcitonin gene-related peptide, sclerostin, and platelet glycoprotein IIb/IIIa.

22. The method according to claim 1, wherein the antigen-binding protein is selected from the group consisting of abciximab, adalimumab, alemtuzumab, basiliximab, belimumab, bevacizumab, brentuximab vedotin, canakinumab, cetuximab, certolizumab pegol, daclizumab, denosumab, eculizumab, efalizumab, gemtuzumab, golimumab, ibritumomab tiuxetan, infliximab, ipilimumab, muromonab-CD3, natalizumab, nivolumab, ofatumumab, omalizumab, palivizumab, panitumumab, ranibizumab, rituximab, tocilizumab, tositumomab, trastuzumab, ustekinumab, vedolizumab, and a biosimilar of any of the foregoing.

23. The method according to claim 1, wherein the antigen-binding protein comprises an antigen-binding region comprising an amino acid sequence selected from the group consisting of SEQ ID NOS: 1-8.

24. The method according to claim 1, wherein the amount of reduced antigen-binding protein molecules is measured using non-reduced capillary electrophoresis with sodium dodecyl sulfate.

25. The method according to claim 1, further comprising a step of cation exchange chromatography.

26. The method of claim 1, comprising (1) a Protein A chromatography step, (2) a viral inactivation step; (3) a depth filtration step; and (4) an incubation step for at least four hours.

27. The method of claim 26, further comprising (5) a cation exchange chromatography step; and one or more of (6) a salt-intolerant interaction chromatography step; (7) a virus filtration step; and (8) ultrafiltration and/or diafiltration.

28. The method of claim 1, wherein the amount or relative amount of reduced antigen-binding protein molecules is determined using non-reduced capillary electrophoresis with sodium dodecyl sulfate (nrCE-SDS).

29. A method of producing an aqueous formulation of an antigen-binding protein comprising
a) contacting an aqueous solution comprising antigen-binding protein molecules with a charged depth filter to form a filtrate,
b) incubating the filtrate for at least four hours, wherein the percentage of reduced antigen-binding protein molecules in the filtrate after the incubating step when compared to the percentage of reduced antigen-binding protein molecules observed in the aqueous solution prior to the contacting step is decreased by 20% as determined by non-reduced capillary electrophoresis with sodium dodecyl sulfate (nrCE-SDS);
c) contacting the filtrate after the incubating step with a protein A column.

30. The method of claim 29, wherein the antigen-binding protein is an IgG antibody.

31. The method according to claim 30, wherein the antibody is an IgG1 antibody with a Kappa light chain, or an IgG1 antibody with a Lambda light chain.

32. A method of enhancing re-oxidization of an antigen-binding protein comprising
a) contacting an aqueous solution comprising antigen-binding protein molecules with a charged depth filter to form a filtrate;
b) incubating the filtrate for at least four hours, wherein the re-oxidation of the antigen-binding protein molecules in the filtrate when compared to a level of re-oxidized antigen-binding molecules in the aqueous solution prior to the contacting step is increased two-fold as determined by non-reduced capillary electrophoresis with sodium dodecyl sulfate (nrCE-SDS); and,
c) contacting the filtrate after the incubating step with a protein A column.

33. The method of claim 32, wherein the antigen-binding protein is an IgG antibody.

34. The method according to claim 33, wherein the antibody is an IgG1 antibody with a Kappa light chain, or an IgG1 antibody with a Lambda light chain.

35. A method of producing an aqueous formulation of an antigen-binding protein comprising
(a) contacting an aqueous solution comprising antigen-binding protein molecules with a charged depth filter comprising a copper ion to form a filtrate, and
(b) incubating the filtrate for at least four hours, wherein the percentage of reduced antigen-binding protein molecules in the filtrate after the incubating step is decreased by at least 20% when compared to the percentage of reduced antigen-binding protein molecules observed in the aqueous solution prior to the contacting step.

36. The method of claim 35, wherein the antigen-binding protein is an IgG antibody.

37. The method according to claim 36, wherein the antibody is an IgG1 antibody with a Kappa light chain, or an IgG1 antibody with a Lambda light chain.

38. A method of enhancing re-oxidization of an antigen-binding protein comprising
(a) contacting an aqueous solution comprising antigen-binding protein molecules with a charged depth filter comprising a copper ion to form a filtrate; and
(b) incubating the filtrate for at least four hours, wherein the re-oxidation of the antigen-binding protein molecules in the filtrate is increased at least two-fold after the contacting step when compared to a level of re-oxidized antigen-binding molecules in the aqueous solution prior to the contacting step.

39. The method of claim 38, wherein the antigen-binding protein is an IgG antibody.

40. The method according to claim 39, wherein the antibody is an IgG1 antibody with a Kappa light chain, or an IgG1 antibody with a Lambda light chain.

* * * * *